United States Patent [19]
Creely et al.

[11] Patent Number: 5,952,210
[45] Date of Patent: Sep. 14, 1999

[54] NUCLEIC ACIDS AND EXPRESSION VECTORS ENCODING HUMAN LEUKOTIENE $C_4$ SYNTHASE

[75] Inventors: David Paul Creely, O'Fallon; Scott David Hauser, St. Louis; Dean James Welsch, St. Peters; Gwen Grabowski Krivi, Frontenac, all of Mo.

[73] Assignee: G. D. Searle & Company, Skokie, Ill.

[21] Appl. No.: 08/254,354

[22] Filed: Jun. 3, 1994

[51] Int. Cl.$^6$ .............................. C12N 9/10; C12N 15/54
[52] U.S. Cl. ................. 435/193; 435/325; 435/320.1; 435/254.2; 435/252.3; 536/23.2; 536/24.31; 536/24.33
[58] Field of Search .................. 435/193, 320.1, 435/254.2, 252.3, 325; 536/23.2, 24.31, 24.33

[56] References Cited

U.S. PATENT DOCUMENTS 5,244,805  9/1993  Miller .................................. 435/320.1

OTHER PUBLICATIONS

Knoth, et al. *Nucleic Acids Research*, 16, (1988), "Highly degenerate, inosine–containing primers specifically amplify rear cDNA using the polymerase chain reaction".

McPherson, et al. M. J. McPherson, et al., "PCR with highly degenerate primers", in PCR—A Practical Approach, Chapter 11, Oxford University Press, 1991.

Nicholson, et al. *Proc. Natl. Acad. Sci. USA*, 90:2015–2019 (1993) "Purification to homogeneity and the N–terminal sequence of human leukotriene $C_4$ synthase: A homodimeric glutathione S–transferase composed of 18–kDa subunits".

Lathe, et al., *J. Mol. Biol.,* (1985), 183:1–12.

Sambrook et al., *Molecular Cloning: A Laboratory Manual,* Cold Spring Harbor Press, 1989, Chapter 11.

*Primary Examiner*—Keith D. Hendricks
*Attorney, Agent, or Firm*—Fitzpatrick, Cella, Harper & Scinto

[57] ABSTRACT

DNAs which encode human $LTC_4$ synthase and expression vectors comprising such DNAs are provided. DNAs encoding human $LTC_4$ synthase may be used in assay methods of the invention for detecting $LTC_4$ synthase inhibitors. Nucleic acid probes capable of identifying cDNAs and/or genomic DNAs encoding LTC4 synthase, as well as $LTC_4$ antisense oligonucleotides and analogs which may be administered to viable cells to inhibit production of $LTC_4$ synthase are also provided.

15 Claims, 6 Drawing Sheets

```
                              B
                              p
                              u
      E                       1
      cF    B                 1
      os    s                 0
      Ri    i                 2
      II    I                 I
       /
     GAATTCGGCACGAGGAGCAGCAGACGGGGCTAAGCGTTCCCCAGCTCGCCTTCACACACA
  1  ------------+------------+------------+------------+------------+------------+ 60
     CTTAAGCCGTGCTCCTCGTCGTCTGCCCCGATTCGCAAGGGGTCGAGCGGAAGTGTGTGT

B         K
               a         p
               n         n
               I         I
     GCCCGTGCCACCACACCGACGGTACCATGAAGGACGAGGTAGCTCTACTGGCTGCTGTCA
 61  ------------+------------+------------+------------+------------+------------+ 120
     CGGGCACGGTGGTGTGGCTGCCATGGTACTTCCTGCTCCATCGAGATGACCGACGACAGT
                                     M   K   D   E   V   A   L   L   A   A   V   T -

S                           E
                                         s                           c
                                         e               B           o
                              B          8               s           o
                              s      S   P3              s           1
                              p      f   s8              H           0
                              M      c   t7              I           9
                              I      I   II                          I
                                         /
     CCCTCCTGGGAGTCCTGCTGCAAGCCTACTTCTCCCTGCAGGTGATCTCGGCGCGCAGGG
121  ------------+------------+------------+------------+------------+------------+ 180
     GGGAGGACCCTCAGGACGACGTTCGGATGAAGAGGGACGTCCACTAGAGCCGCGCGTCCC
      L   L   G   V   L   L   Q   A   Y   F   S   L   Q   V   I   S   A   R   R   A -

C
              B                      f
              s                      r           A                       A
              r                      1           v                       c
              B                      0           a                       c
              I                      I           I                       I
     CCTTCCGCGTGTCGCCGCCGCTCACCACCGGCCCACCCGAGTTCGAGCGCGTCTACCGAG
181  ------------+------------+------------+------------+------------+------------+ 240
     GGAAGGCGCACAGCGGCGGCGAGTGGTGGCCGGGTGGGCTCAAGCTCGCGCAGATGGCTC
      F   R   V   S   P   P   L   T   T   G   P   P   E   F   E   R   V   Y   R   A -
```

FIG. 1-1

```
                B
                s
                p                                                                C
                B1                              N                                f
                a2          S        P        S       s                 P        r       N
                n8          f        s        c       p                 f        l       a
                I6          c        t        a       B                 l        0       e
                II          I        I        I       I                 M        I       I
                /                                                       I
           CCCAGGTGAACTGCAGCGAGTACTTCCCGCTGTTCCTCGCCACGCTCTGGGTCGCCGGCA
      241  ---------+---------+---------+---------+---------+---------+ 300
           GGGTCCACTTGACGTCGCTCATGAAGGGCGACAAGGAGCGGTGCGAGACCCAGCGGCCGT

Q   V   N   C   S   E   Y   F   P   L   F   L   A   T   L   W   V   A   G   I  -

B
                 B                                                            s
                 s                                                            s
                 p                                              A             H
                 H                                              c             I
                 I                                              c             I
                                                                I
           TCTTCTTTCATGAAGGGGCGGCGGCCCTGTGCGGCCTGGTCTACCTGTTCGCGCGCCTCC
      301  ---------+---------+---------+---------+---------+---------+ 360
           AGAAGAAAGTACTTCCCCGCCGCCGGGACACGCCGGACCAGATGGACAAGCGCGCGGAGG

F   F   H   E   G   A   A   A   L   C   G   L   V   Y   L   F   A   R   L   R  -

B               B                       N          B B
                             s               p                       s          s s
                             s               u                 B     p          s s
                             H               l                 a     B          H H
                             I               0                 n     I          I I
                             I               I                 I     I          I I
           GCTACTTCCAGGGCTACGCGCGCTCCGCGCAGCTCAGGCTGGCACCGCTGTACGCGAGCG
      361  ---------+---------+---------+---------+---------+---------+ 420
           CGATGAAGGTCCCGATGCGCGCGAGGCGCGTCGAGTCCGACCGTGGCGACATGCGCTCGC

Y   F   Q   G   Y   A   R   S   A   Q   L   R   L   A   P   L   Y   A   S   A  -

B
              s
              s                              H                                          G
              H                              a                                          d
              I                              e                                          i
              I                              I                                          I
                                             I                                          I
           CGCGCGCCCTCTGGCTGCTGGTGGCGCTGGCTGCGCTCGGCCTGCTCGCCCACTTCCTCC
      421  ---------+---------+---------+---------+---------+---------+ 480
           GCGCGCGGGAGACCGACGACCACCGCGACCGACGCGAGCCGGACGAGCGGGTGAAGGAGG

```
       X       B
       GmB     s                           B
       Edas    s                           Bs                 D    B
       aiIi    H                           ep                 s    s
       eIIE    I                           tE                 a    a
       IIII                                II                 I    I
       //                                  /
       CGGCCGCGCTGCGCGCCGCGCTCCTCGGACGGCTCCGGACGCTGCTGCCGTGGGCCTGAG
481    ------------+------------+------------+------------+------------+ 540
       GCCGGCGCGACGCGCGGCGCGAGGAGCCTGCCGAGGCCTGCGACGACGGCACCCGGACTC

A   A   L   R   A   A   L   G   R   L   R   T   L   L   P   W   A   *

E
            c
            o
            o                                                   N
            1                                                   sP
       S    0    A  S                    ES G                   pv    A  S
       t    9    v  m                    aa s                   Bu    v  m
       y         a  a                    rp u                   II    a  a
       I    I    I  I                    II I                   II    I  I
                                         /                      /
       ACCAAGGCCCCCGGGCCGACGGAGCCGGGAAAGAAGAGCCGGAGCCTCCAGCTGCCCCGG
541    ------------+------------+------------+------------+------------+ 600
       TGGTTCCGGGGGCCCGGCTGCCTCGGCCCTTTCTTCTCGGCCTCGGAGGTCGACGGGGCC

H
                          a
                          e
                          I
                          I
       GGAGGGGCGCTCGCTTCCGCATCCTAGTCTCTATCATTAAAGTTCTAGTGACCGAGAAAA
601    ------------+------------+------------+------------+------------+ 660
       CCTCCCCGCGAGCGAAGGCGTAGGATCAGAGATAGTAATTTCAAGATCACTGGCTCTTTT

T
       a
       q
       I               AX
       I               vh
       -               ao
       1               II
                       /
       AAAAAAAAAAAAAAAAAAAAACTCGAG
661    ------------+------------+---  685
       TTTTTTTTTTTTTTTTTTTTTGAGCTC
```

FIG. 1-3

NUCLEIC ACIDS AND EXPRESSION VECTORS ENCODING HUMAN LEUKOTIENE C$_4$ SYNTHASE

FIELD OF THE INVENTION

The present invention generally relates to leukotrienes (LTs), especially leukotriene C$_4$ (LTC$_4$), and more particularly to DNAs encoding human LTC$_4$ synthase, to methods for producing recombinant human LTC$_4$ synthase in host cells, methods for in vivo inhibition of production of LTC$_4$ synthase and assay methods employing recombinant LTC$_4$ synthase for detecting LTC$_4$ synthase inhibitor activity.

BACKGROUND OF THE INVENTION

The production of leukotrienes (LTs) is an important physiological response to immunological challenge. Leukotrienes C$_4$, D$_4$ and E$_4$ (LTC$_4$, LTD$_4$ and LTE$_4$) play a very significant role in the pathophysiology of several inflammatory diseases, especially chronic asthma and allergic rhinitis. LTC$_4$ synthase is a glutathione-S-transferase which uniquely catalyzes the synthesis of LTC$_4$ from LTA$_4$ and reduced glutathione. LTC$_4$ is a peptidoleukotriene having a cysteinyl-glycine (Cys—Gly) moiety which is derivatized with gamma-glutamic acid. Cleavage of the gamma-glutamic acid residue yields LTD$_4$ containing the dipeptide Cys—Gly. Dipeptidase cleavage of the glycine residue from LTD$_4$ yields LTE$_4$.

LTC$_4$ and LTD$_4$ are potent bronchoconstrictors which act on smooth muscle cells in the lung. These peptidoleukotrienes are released endogenously in the lung tissue of asthmatics upon exposure to specific allergens and induce many of the phenomena associated with asthma, including pulmonary smooth muscle contraction, vasoconstriction, increased vascular permeability, slow mucociliary clearance, and increased mucus secretion, when these leukotrienes are administered exogenously.

Because the glutathione-S-transferase, LTC$_4$ synthase, is essential for the production of LTC$_4$ from which are derived LTD$_4$ and LTE$_4$, and because elevated LTC$_4$ and LTD$_4$ levels are associated with potent bronchoconstriction in response to immunological challenge, it would be very desirable to be able to identify LTC$_4$ synthases inhibitor compounds which can selectively inhibit production of LTC$_4$, LTD$_4$ and LTE$_4$.

LTC$_4$ synthase is a membrane-bound glutathione S-transferase activity that is distinct from all other glutathione S-transferases and appears to be exclusively committed to the biosynthesis of LTC$_4$. Human LTC$_4$S is composed of a single 18-kDa polypeptide that is functionally active as a homodimer. The purification to homogeneity and partial amino acid sequence have been reported for human LTC$_4$S from the human monocytic leukemia cell line THP-1 by D. W. Nicholson et al., *Proc. Natl. Acad. Sci.* USA 90, 2015–2019 (1993). However, the complete amino acid sequence and nucleotide sequence for LTC$_4$ synthase were heretofore unknown. Moreover, the purification is difficult and the scale-up in production necessary to obtain large quantities of LTC$_4$ synthase necessary for large scale LTC$_4$ inhibitor screening assays is problematic.

It would be very advantageous to provide DNAs which encode human LTC$_4$ synthase and to provide expression vectors comprising such DNAs, which vectors, when introduced into suitable host cells, direct the production of recombinant human LTC$_4$ synthase. It would also be very beneficial to be able to utilize recombinant human LTC$_4$ synthase, and host cells capable of making recombinant LTC$_4$ synthase, in screening assays to detect compounds capable of inhibiting LTC$_4$ synthase.

SUMMARY OF THE INVENTION

The present invention provides nucleic acids which encode human LTC$_4$ synthase, expression vectors comprising a DNA segment which codes for human LTC$_4$ synthase and recombinant LTC$_4$ synthase polypeptide. The present invention also provides nucleic acid fragments comprising at least a portion of a nucleic acid which encodes LTC$_4$ synthase, which nucleic acid fragments are useful as hybridization probes for the detection and isolation of cDNAs and/or genomic DNAs encoding LTC$_4$ synthase.

The present invention also provides assay methods for detecting compounds which are capable of inhibiting LTC$_4$ synthase activity. In accordance with LTC$_4$ synthase inhibitor assays of the invention, recombinant human LTC$_4$ synthase is combined with a compound which is a putative or known inhibitor of LTC4 synthase, and the amount of LTC$_4$ synthase activity remaining, if any, is determined, relative to a substantially identical amount of LTC$_4$ synthase activity which was not combined with a known or putative LTC$_4$ synthase inhibitor compound.

The present invention further provide antisense oligonucleotides and analogs thereof having a nucleotide sequence which is complementary to a portion of a sense strand of an LTC$_4$ synthase gene. The antisense oligonucleotides of the invention are capable of binding to, and preventing the production of polypeptides from, mRNAs coding for LTC$_4$ synthase.

BRIEF DESCRIPTION OF THE DRAWINGS

FIG. 1 shows a nucleotide sequence which encodes human LTC$_4$ synthase and shows the amino acid sequence thereof;

DETAILED DESCRIPTION OF THE INVENTION

Figure 2:
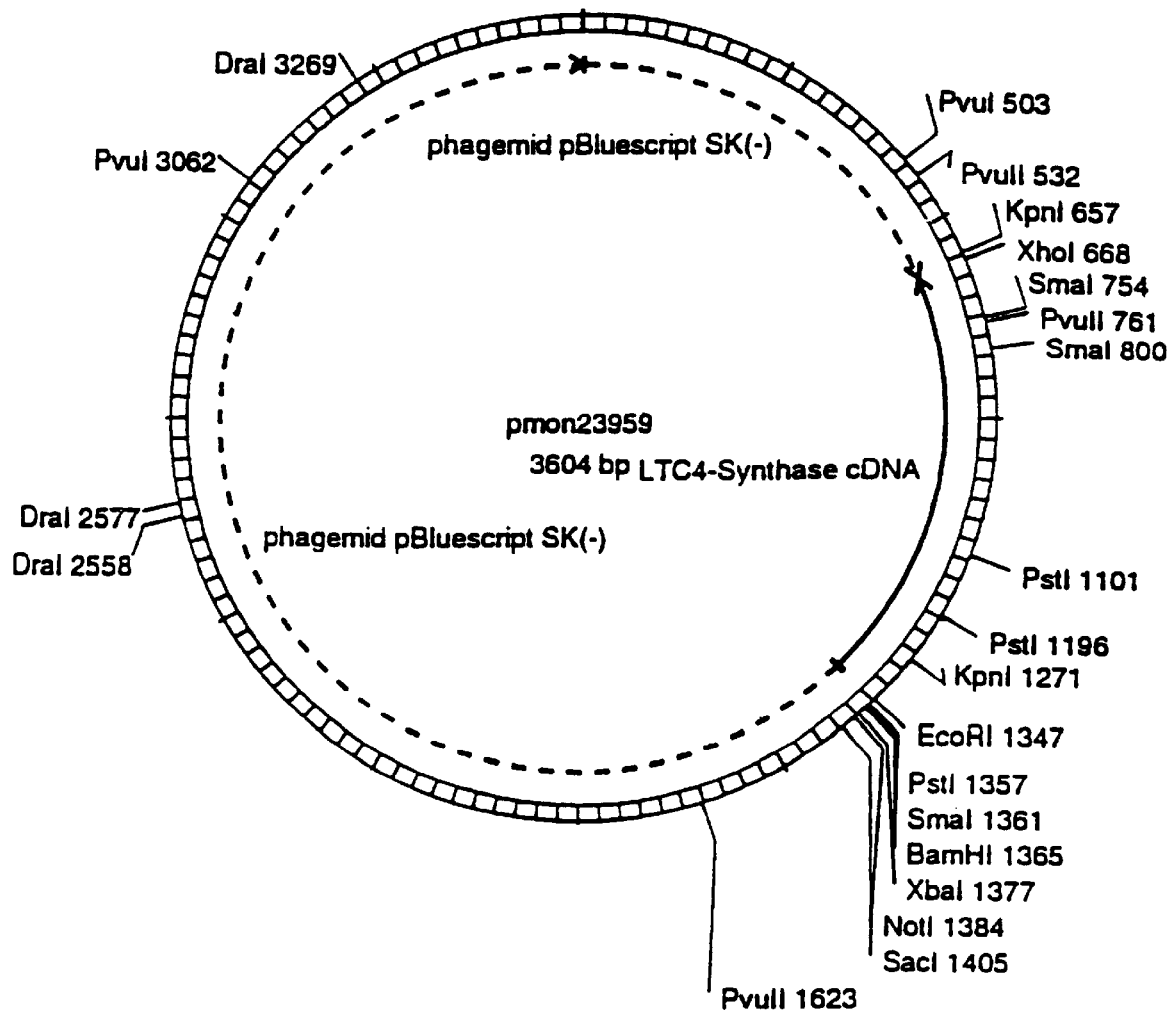
FIG. 2 is a restriction map of plasmid pMON23959 which corresponds to phagemid pBluescript SK(−) containing an EcoRI-XhoI insert which is a human LTC$_4$ synthase cDNA.
Figure 3:
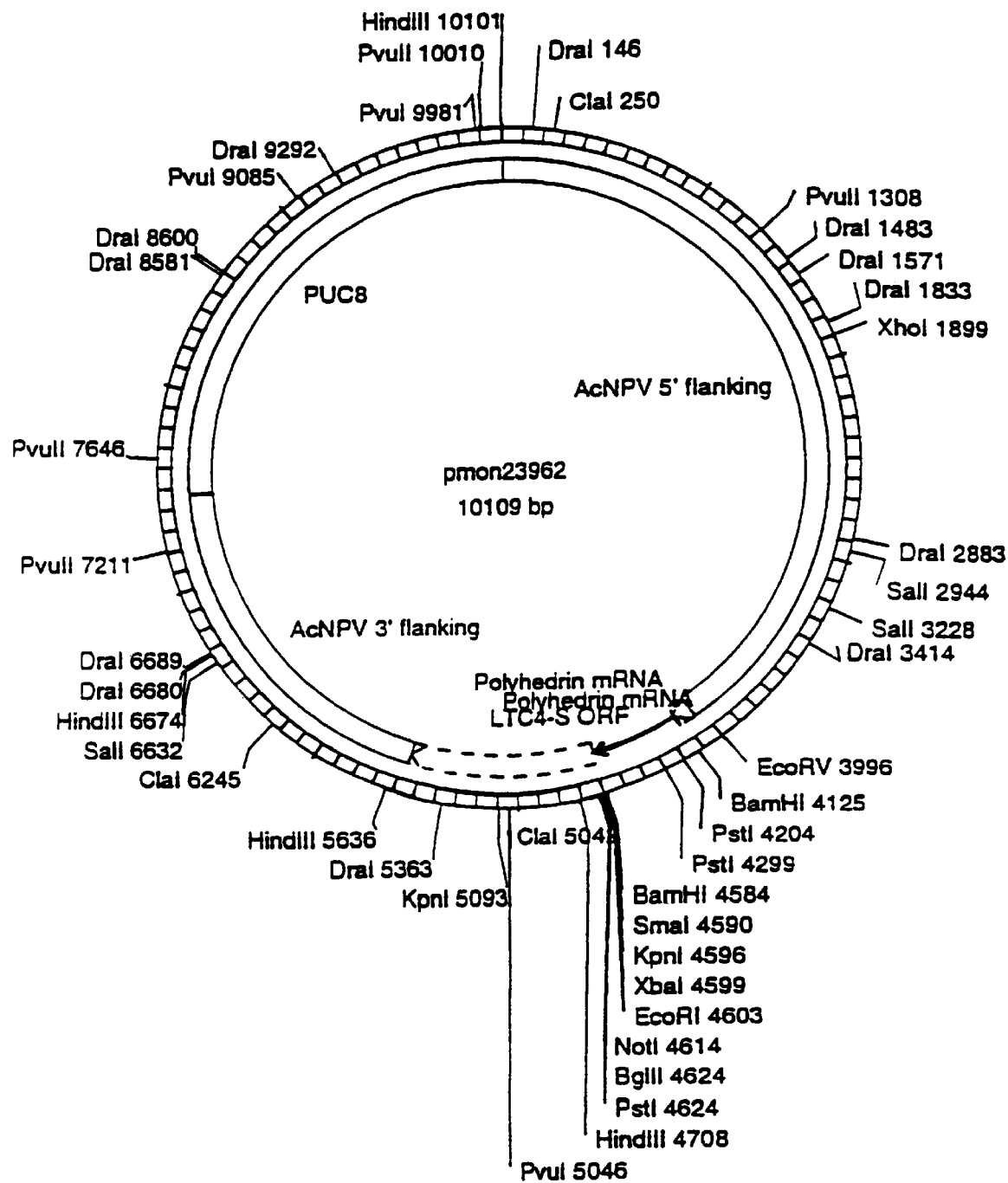
FIG. 3 is a restriction map of plasmid pMON23962 which corresponds to baculovirus expression vector pVL1393 containing a BamHI insert encoding the open reading frame (ORF) of human LTC$_4$ synthase gene.
Figure 4:
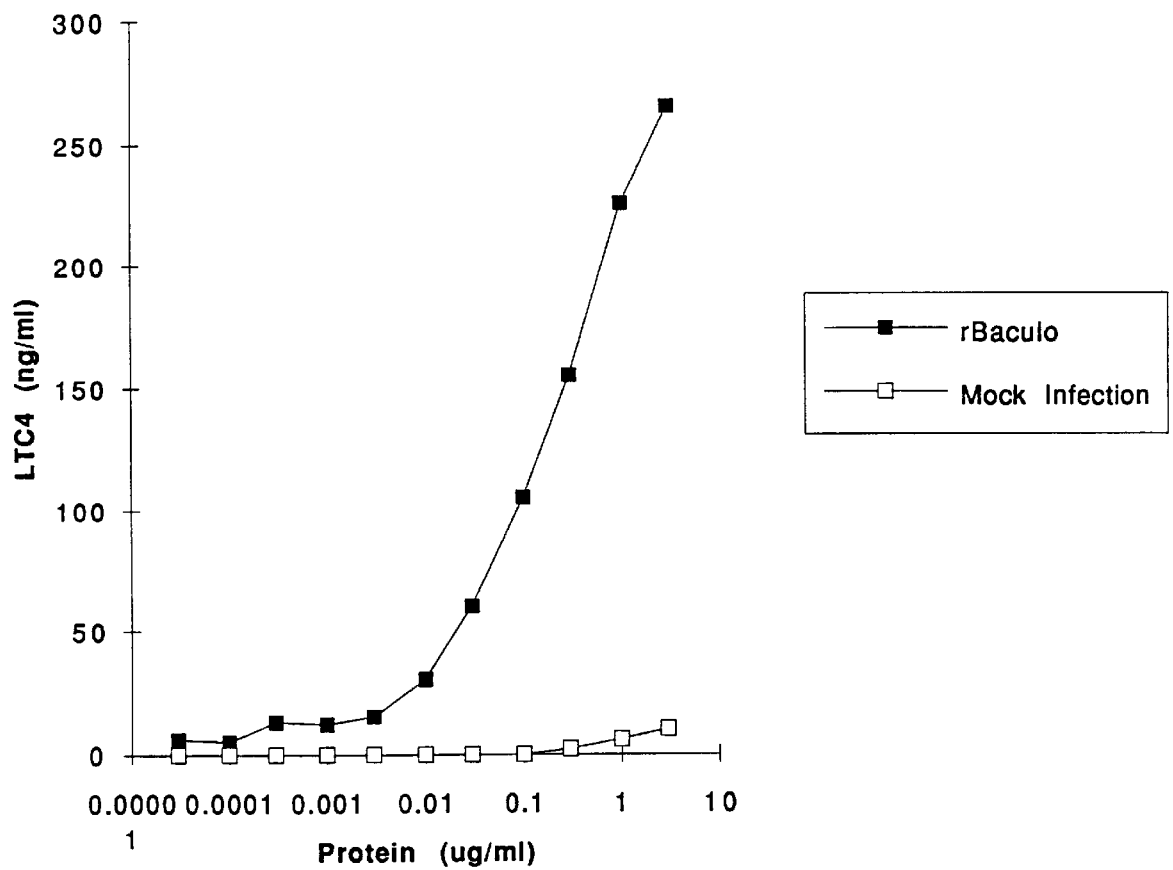
FIG. 4 is graph depicting the dose-dependent expression of human recombinant LTC$_4$ synthase activity in insect cells harboring plasmid pMON23962.

In one of its aspects, the present invention is directed to a nucleic acid which comprises a DNA segment which encodes at least a portion of human leukotriene C4 synthase, which nucleic acid is substantially free from nucleic acids not containing a DNA segment which encodes at least a portion of human LTC$_4$ synthase, the DNA segment which encodes at least a portion of human LTC$_4$ synthase being selected from the group of:

(i) a nucleic acid sequence represented by nucleotides 7–679, inclusive, or a nucleic acid sequence represented by nucleotides 87–539, inclusive, of Sequence ID No. 1;

(ii) a nucleotide sequence which is complementary to a nucleotide sequence of (i);

(iii) fragments of (i) or (ii) which are at least 17 bases in length and which will selectively hybridize to a nucleic acid encoding human LTC$_4$ synthase; and (iv) nucleotide sequences which are at least about 17 bases in length and which will selectively hybridize, under stringent hybridization conditions, to a cDNA or genomic DNA encoding human $LTC_4$ synthase.

The present invention also concerns a DNA which is an $LTC_4$ synthase encoding DNA, the DNA comprising (1) a promoter segment of a first gene, which segment comprises the promoter and transcription initiation site of the first gene, (2) a terminator segment of a second gene, which may be the same or different from the first gene, which terminator segment comprises a polyadenylation signal encoding, a polyadenylation site encoding segment and a transcription termination signal, the terminator segment of the second gene being oriented, with respect to the direction of transcription from the promoter segment of the first gene, operatively for termination of transcription at said transcription termination site of the terminator segment; and (3) a DNA segment which encodes a human $LTC_4$ synthase oriented and positioned, between the promoter segment of the first gene and termination segment of the second gene, operatively for transcription of the $LTC_4$ synthase encoding DNA.

In another of its aspects, the present invention involves host cells which harbor an expression vector comprising a DNA encoding human $LTC_4$ synthase and capable of directing the expression of $LTC_4$ synthase activity by the host cell.

In a further of its aspects, the present invention is directed to a recombinant human leukotriene $C_4$ synthase having the following amino acid sequence which corresponds to SEQ ID No. 2 herein:

activity wherein the $LTC_4$ synthase activity is provided by recombinant human $LTC_4$ synthase. Thus, in another of its aspects, the invention involves an in vitro assay for detecting an $LTC_4$ synthase inhibitor compound which method comprises:

a) combining, in a compartment containing an aqueous medium, (i) recombinant human $LTC_4$ synthase and (ii) a compound which is a putative $LTC_4$ synthase inhibitor compound;

b) adding $LTA_4$ and, if necessary, reduced glutathione to the aqueous medium;

c) incubating the aqueous medium for a predetermined amount of time;

d) determining the amount of $LTC_4$ in the compartment containing recombinant human $LTC_4$ synthase and the putative $LTC_4$ synthase inhibitor compound, relative to a compartment which was treated substantially identically to said compartment of step (a), but which is devoid of a putative $LTC_4$ synthase inhibitor compound.

The term "$LTC_4$ synthase" as used herein refers to a polypeptide having the ability to catalyze the synthesis of $LTC_4$ from $LTA_4$ and reduced glutathione, which catalytic ability is in common with a naturally occurring $LTC_4$ synthase. By the term "recombinant $LTC_4$ synthase" is meant a polypeptide having the amino acid sequence represented in Sequence ID No. 2, which polypeptide is produced in a host cell harboring a heterologous DNA which encodes $LTC_4$ synthase.

```
Met Lys Asp Glu Val Ala Leu Leu Ala Ala Val Thr Leu Leu Gly Val
 1               5                  10                  15

Leu Leu Gln Ala Tyr Phe Ser Leu Gln Val Ile Ser Ala Arg Arg Ala
            20                  25                  30

Phe Arg Val Ser Pro Pro Leu Thr Thr Gly Pro Pro Glu Phe Glu Arg
        35                  40                  45

Val Tyr Arg Ala Gln Val Asn Cys Ser Glu Tyr Phe Pro Leu Phe Leu
    50                  55                  60

Ala Thr Leu Trp Val Ala Gly Ile Phe Phe His Glu Gly Ala Ala Ala
65                  70                  75                  80

Leu Cys Gly Leu Val Tyr Leu Phe Ala Arg Leu Arg Tyr Phe Gln Gly
            85                  90                  95

Tyr Ala Arg Ser Ala Gln Leu Arg Leu Ala Pro Leu Tyr Ala Ser Ala
            100                 105                 110

Arg Ala Leu Trp Leu Leu Val Ala Leu Ala Ala Leu Gly Leu Leu Ala
            115                 120                 125

His Phe Leu Pro Ala Ala Leu Arg Ala Ala Leu Leu Gly Arg Leu Arg
    130                 135                 140

Thr Leu Leu Pro Trp Ala
145                 150
```

In another of its aspects, the present invention entails antisense nucleic acids or antisense oligonucleotides (or oligonucleotide analogs) which are about 12–30 nucleotides in length and have a sequence which is complementary to a nucleic acid segment represented by Seq. ID No. 1 (excluding the 5'- and 3'-terminal restriction endonuclease sites), such that the antisense oligonucleotides of the invention are capable of hybridizing with $LTC_4$-encoding mRNAs and preventing translation of the mRNA into $LTC_4$ synthase or a polypeptide fragment thereof having $LTC_4$ synthase activity.

The present invention also involves an assay for detecting a compound which is capable of inhibiting $LTC_4$ synthase The term "$LTC_4$ synthase encoding nucleic acid" or "nucleic acid encoding the $LTC_4$ structural gene" refers to a single-stranded or double stranded nucleic acid having a coding sequence of nucleotides which codes for the amino acid sequence of SEQ ID No. 2. A particularly preferred $LTC_4$ synthase encoding nucleic acid is a nucleic acid comprising the nucleotide sequence represented by nucleotides 87–539 of sequence ID No. 1.

The nucleotide bases are referred to by their well known and commonly used designations A,T,G and C. The abbreviations designate the nucleoside bases adenine, thymine, guanosine cytidine, respectively. With respect to nucleic acids which are RNAs, the nucleic acid has a ribose backbone, rather than a deoxyribose backbone, and the thymine (T) is replaced by uracil (U).

By "stringent conditions" is meant nucleic acid hybridization in 50% formamide; 4X SSPE; 0.1% SDS; 5X Denhardt's Reagent ; 100 µg/ml T-RNA at 42° C. for 16 hours, followed by washing conditions of 0.1X SSPE at 65° C. for 1 hour.

(20X SSPE=174.0 g NaCl, 27.6 g $NaH_2PO_4 \cdot H_2O$, 7.4 g EDTA/1000 ml, pH 7.4); (50X Denhardt's Reagent=5 g ficoll, 5 g polyvinylpyrrolidone; 5 g bovine serum albumin/1000 ml.)

The amino acids referred to herein are the naturally occurring L-amino acids identified by either the single-letter or three-letter designations:

| Asp | D | aspartic acid | Ile | I | isoleucine |
|-----|---|---------------|-----|---|------------|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

An "expression vector" or "transforming DNA" of the invention as used herein refers to a DNA which contains a promoter segment which is capable of driving transcription of a DNA segment which encodes an $LTC_4$ synthase structural gene; a transcription termination segment having a transcription termination codon, a polyadenylation site and a polyadenylation sequence; and a DNA segment which encodes an $LTC_4$ synthase structural gene which is oriented and operatively associated with the promoter segment and transcription termination segment for transcription of the $LTC_4$ synthase encoding segment. By "oriented and operatively associated" is meant that the promoter segment is located upstream from the $LTC_4$ synthase encoding segment; that the transcription termination segment is located downstream from the $LTC_4$ synthase encoding segment such that transcription from the promoter provides a transcript encoding $LTC_4$ synthase; that the 3'-end of the promoter segment is linked by a phosphodiester bond to the 5'-end of the $LTC_4$ synthase encoding segment and the 3'-end of the $LTC_4$ synthase encoding segment is linked by a phosphodiester bond to the 5'-end of the transcription termination segment. The terms "upstream" and "downstream" thus refer to the direction of transcription (i.e., the 5' to 3' direction) from the promoter driving transcription of the $LTC_4$ synthase encoding DNA.

A nucleic acid encoding human $LTC_4$ synthase may be synthesized based on the nucleotide sequence disclosed herein using either organic synthesis or molecular biological techniques. An $LTC_4$ synthase encoding DNA may be made using a nucleic acid synthesizer, such as an Applied Biosystems Model 380B DNA Synthsizer, by producing double stranded DNA segments (preferably having single stranded ends) from sets of oligonucleotides which can be hybridized and ligated. Individual DNA segments corresponding to one segment of the $LTC_4$ synthase coding region may then be hybridized and ligated to DNA segments corresponding to a contiguous segment until a full length double stranded DNA encoding the $LTC_4$ synthase gene product is obtained.

The oligonucleotides can be synthesized in sizes up to 100 bases in length or greater. A computer program (e.g., PC Gene, by Inteligenics Co., Mountain View, Calif.) may be used for searching and identifying restriction sites contained within a nucleotide sequence encoding $LTC_4$ synthase, which restriction sites can be used to hybridize segments in the correct orientation for ligation into the full length $LTC_4$ encoding DNA. It may be desirable to modify the $LTC_4$ encoding sequence to change one or more codons so as to introduce a unique restriction site without changing the amino acid sequence of the gene product. Such techniques for building double stranded DNAs are well known and described in detail, for example in Davis et al., Basic Methods in Molecular Biology, Elsevier Science Publ. Co., Inc., New York (1986).

A DNA of the present invention which is a cDNA encoding $LTC_4$ synthase may be obtained using recombinant DNA techniques. Messenger RNA may be isolated from cells which express $LTC_4$ synthase and used to construct a cDNA library using a suitable cDNA vector such as lambda ZAP or other lambda phage. A preferred cell line which expresses elevated levels of $LTC_4$ synthase mRNA is the human monocytic leukemia cell line THP1 (ATCC # TIB 202); S. Tsuchiya, et al., Int. J. Cancer 26, 171–176 (1990). Competent bacteria cells are transformed with the cDNA phage library and grown for identification, by nucleic acid hybridization, of those cell colonies which have a cDNA encoding the $LTC_4$ gene. The basic techniques and strategies for preparing DNA libraries, and oligonucleotide probes, as well as for screening by nucleic acid hybridization and sequencing nucleic acid segments, are well known to the person of ordinary skill in the art. See, for example, Sambrook et al., Molecular Cloning: A Laboratory Manual (Cold Spring Harbor Laboratory Press, 1989).

Also, DNAs of the present invention may be prepared from mRNA using RT-PCR (reverse transcriptase-polymerase chain reaction) [PCR Protocols: A Guide to Methods and Applications, Innis, M., et al., Academic Press (1990), San Diego, Calif.], employing a pair of oligonucleotide primers, one of which is selected from the flanking 5'-untranslated region of the sense strand of an $LTC_4$ synthase encoding DNA and the other primer from the pair being selected from a segment which is complementary to the 3'-untranslated region of the sense strand of a DNA which encodes $LTC_4$ synthase. Among the pairs of oligonucleotide primers which may be used are DNAs comprising a single-stranded sequence which is about 17 nucleotides or greater in length, preferably 25–50 nucleotides in length, wherein the first primer of the pair comprises a single stranded sequence which is a fragment of the sequence represented by nucleotides 7 to 86 of sequence ID #1 and a second primer of the pair comprises a single-stranded sequence of about 17 nucleotides or greater in length, preferably about 20–50 nucleotides in length, which corresponds to nucleotides 7 to 149 of SEQ ID No. 3 (i.e., is complementary to the nucleotide sequence represented by nucleotides 537 to 679 of seq. ID No. 1). The oligonucleotide primers may advantageously comprise additional nucleotide sequences to provide one or more restriction endonuclease sites to facilitate cloning into an expression vector after amplification by RT-PCR.

DNAs of the present invention which are at least 17 nucleotides in length, preferably at least about 25 nucleotides in length and more preferably at least about 40 nucleotides in length, and which have a sequence which corresponds to the $LTC_4$ synthase sequence disclosed herein, may be used as probes for screening by nucleic acid hybridization. Once a full length cDNA (i.e., spanning the entire 450 nt $LTC_4$ synthase encoding region, and optionally into the 5'- and/or 3'- untranslated regions of the $LTC_4$ synthase gene) is obtained and its nucleotide sequence confirmed, such full length cDNA may be used to isolate and clone LTC$_4$ synthase genes from other species.

In general prokaryotes are preferred for cloning of DNA sequences in constructing the vectors useful in the invention. A commercially available *E. coli* strain, XL1 Blue cells (Stratagene, La Jolla, Calif.) is particularly useful. Other microbial strains which may be used include, but are not limited to *E. coli* strains such as *E. coli* B, *E. coli* K 12 strain 294 (ATTC No. 31446) and *E. coli* X1776 (ATTC No. 31537).

With respect to expression of a DNA of the present invention prokaryotes may be employed, such as *E. coli* W3110 (F—, λ—, prototrophic, ATTC No. 27325), *E. coli* strain, XL1 Blue cells, bacilli such as *Bacillus subtilus*, and other enterobacteriaceae such as *Salmonella typhimurium* or *Serratia marcescens*, and various Pseudomonas species.

An expression vector or transforming DNA of the invention which may be used in prokaryotic cells comprises a promoter which is capable of driving transcription of a DNA segment which encodes the LTC$_4$ synthase structural gene; a DNA sequence which encodes an LTC$_4$ synthase structural gene; and a prokaryote ribosome binding site therebetween; wherein the DNA encoding the LTC$_4$ synthase structural gene is oriented and operatively associated with the promoter and the ribosome binding segment for expression in a prokaryotic host cell of LTC$_4$ synthase.

Prokaryotic expression vectors comprising a suitable ribosome binding site located upstream from the DNA segment encoding a heterologous polypeptide and generally close to the start codon are well known in the art. U.S. Pat. No. 5,232,840 discloses presently preferred ribosome binding sites which are capable of providing enhanced protein production in prokaryotes.

While it is not essential, optionally a prokaryotic expression vector may comprise a transcription termination segment oriented and operatively associated with the DNA segment encoding LTC$_4$ synthase (i.e., positioned downstream and joined by a phosphodiester bond to the 3'-end of the LTC$_4$ synthase encoding segment). Suitable prokaryotic transcription termination segments comprising a transcription termination signal include the T4 gene 23 terminator, Parker et al., *J. Mol. Biol.* 180, 399–416 (1984); the P22 gene ant terminator, Berget et al., *J. Mol. Biol.* 164, 561–572; the Col E 1 terminator, Olins et al., *Cell,* 26, 205–214 (1981), as well as other transcription terminator segments from bacterial genes or bacteriophage genes. See Holmes et al., *Cell,* 32, 1029–1032 (1983).

An expression vector or transforming DNA of the invention preferably may include elements for its selection and replication in bacteria, especially *E. coli*. This facilitates production of large quantities of DNA by replication in bacteria. A preferred DNA of the invention is a plasmid which includes a segment comprising the origin of replication and ampicillin resistance or tetracycline-resistance gene of the plasmid pBR322. A DNA of the invention may also comprise a selectable marker gene which is functional in a host cell harboring the expression vector to allow cells harboring the expression vector to be distinguished from cells which do not harbor such a DNA as is known in the art. For example, *E. coli* is typically transformed using pBR322, a plasmid derived from an *E. coli* species (Bolivar, et al., *Gene* 2:95 (1977)). pBR322 contains genes for ampicillin and tetracycline resistance and thus provides easy means for identifying transformed cells. The pBR322 plasmid, or other microbial plasmid, must also contain, or be modified to contain, promoters which can be used by the microbial organism for expression of its own proteins. Those promoters most commonly used in recombinant DNA contstruction include the β-lactamase (penicillinase) and lactose promoter systems (Chang et al, *Nature,* 275:615 (1978); Itakura, et al, *Science,* 198:1056 (1977); Goeddel, et al, *Nature,* 281:544 (1979)) and a tryptophan (trp) promoter system (Goeddel, et al, *Nucleic Acids Res.,* 8:4057 (1980); EPO Appl. Publ. No. 0036776).

A DNA of the invention which includes an origin of replication or autonomous replication sequence which is functional in a compatible host cell can be maintained as an episomal DNA (closed circular plasmid) after transformation into the host cell. A number of DNA segments comprising origins of replication and/or autonomous replication sequences are known in the art. While these are the most commonly used, other microbial promoters have been discovered and utilized, and details concerning their nucleotide sequences have been published, enabling a skilled worker to ligate them functionally with plasmid vectors (Siebenlist, et al, *Cell,* 20:269 (1980).

Eukaryotic microbes, such as yeast cultures, harboring a DNA of the invention may also be used to express LTC$_4$ synthase. *Saccharomyces cerevisiae* is a commonly used eukaryotic microorganisms, although a number of other strains are commonly available. For expression in Saccaromyces, the plasmid YRp7, for example, (Stinchcomb, et al., *Nature,* 282:39 (1979); Kingsman, et al., *Gene,* 7:141 (1979); Tschemper, et al, *Gene,* 10:157 (1980)) is commonly used. This plasmid already contains the trpl gene which provides a selection marker for a mutant strain of yeast lacking the ability to grow in tryptophan, for example ATCC No. 44076 or PEP4-1 (Jones, *Genetics,* 85:12 (1977)). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., *J. Biol. Chem.,* 255:2073 (1980)) or other glycolytic enzymes (Hess, et al., *J. Adv. Enzyme Reg.,* 7:149 (1968); Holland, et al., *Biochemistry,* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned glyceralehyde-3-phosphate dehydrogenase, and enzymes responsible for maltose and galactose utilization (Holland, ibid.). Any plasmid vector containing yeast-compatible promoter, origin of replication and termination sequences is suitable.

Methylotrophic yeast cells, such as *Pichia pastoris*, Hensenula species, e.g. *H. polymorpha* and Kluyveromyces species, may also be used to express recombinant LTC$_4$ synthase. For example, *P. pastoris* expression vectors are known which contain the promoter of the major alcohol oxidase gene (AOXI) of *P. pastoris* which is highly expressed and easily regulated by the presence of methanol. The construction of *P. pastoris* expression vector is disclosed in U.S. Pat. No. 5,102,789 and in Sreekrishna et al., J. Basic Microbiol., 28, 265–278 (1988). Among other yeast cell expression systems are Kluyveromyces species such as are disclosed in U.S. Pat. No. 4,943,529. Also, Kluyveromyces species are commercially available, such as *K. waltii* (ATCC 56,500), *K. wickeramii* (ATCC 24,178), *K. fragilis* (ATCC 14,424), *K. bulgaricus* (ATCC 16,045) and the like.

Insect cells harboring expression vectors encoding $LTC_4$ synthase may also be employed to express $LTC_4$ synthase encoding DNAs of the invention. Among the commonly used insect expression vectors are the baculoviruses *Autographa californica* nuclear polyhedrosis virus (AcMNPV) and *Bombyx mori* nuclear polyhedrosis virus (BmNPV). *Autographa californica* nuclear polyhedrosis virus is particularly preferred. Insect cells which may used as host cells for the expression include *Spodoptera frugiperda* cells and *Tricoplusia ni* cells. Baculovirus expression vectors and techniques for transfecting insect cells are disclosed in U.S. Pat. Nos. 4,745,051; 5,244,805; 5,278,050; D. R. O'Reilly et al., Baculovirus Expression Vectors: A Laboratory Manual (W. H. Freeman and Company, New York); and M. D. Summers, et al., A Manual of Methods for Baculovirus Vectors and Insect Cell Procedures, Texas Agriculture Experiment Station Bulletin No. 1555. Baculovirus expression vectors are also available from commercial sources such as Pharmingen, Inc., San Diego Calif. Examples 2 and 3 herein describe the cloning into a baculovirus expression vector of a DNA segment encoding $LTC_4$ synthase, and the transfection of, and expression of $LTC_4$ synthase in, *Spodoptera frugiperda* Sf9 cells.

Cultures of mammalian cells may also be used as hosts. Examples of such useful host cell lines are VERO and HeLa cells, Chinese hamster ovary (CHO) cell lines, and W138, BHK, COS-7 and MDCK cell lines. Expression vectors for such cells ordinarily include (if necessary) an origin of replication, a promoter located in front of the genes to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, cytomegalo, Adenovirus 2, RSV, and most frequently Simian Virus 40 (SV40). The early and late promoters of SV40 virus are particularly useful because both are obtained easily from the virus as a fragment which also contains the SV40 viral origin of replication (Fiers, et al., Nature, 273:113 (1978) incorporated herein by reference). Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g. Polyome, Adeno, VSV, BPV, etc.) source, or may be provided by the host cell chromosomal replication mechanism.

If the vector is integrated into the host cell chromosome, the latter is often sufficient. Integration of a DNA of the invention may occur via homologous recombination into the genome of a host cell. Integration can be accomplished by transformation or transfection with vectors which contain one or more DNA segment which are at least about 200 bp in length, which are homologous in sequence to a DNA segment which occurs in the host cell's genome. Methods for causing integration of heterologous DNA into the genomes of eukaryotic cells, including yeast cells, insect cells and mammalian cells are well known in the art and may be accomplished with DNAs of the present invention. See, for example, European Patent Application Publication No. 0 226 752.

The transformation or transfection of eukaryotic and prokaryotic host cells and the culturing of transformed and transfected host cells are routine in the art. Mammalian cells may be transformed by such methods as calcium phosphate co-precipitation, DEAE-dextran procedure, electroporation, lipofection and the like. Yeast cell transformations are generally carried out using the polyethylene glycol method or spheroplast yeast transformation system. Culturing of host cells may be carried out in a variety of commercially available culture media including, but not limited to RPMI 1640, Dulbecco's Modified Eagle's Medium, Ham's F10 Medium, Grace's Medium, and the like, generally supplemented with fetal bovine serum, and optionally growth factors, antibiotics, and the like, as well known in the art.

Recombinant human $LTC_4$ synthase may be isolated from a microsomal fraction of cultured recombinant host cells using conventional biochemical methods, including detergent solubilization, anion or cation exchange chromatography, hydrophobic interaction chromatography and immunoaffinity chromatography. A presently preferred method involves solubilization of $LTC_4$ synthase containing microsomal membrane with 2% taurocholate; anion-exchange chromatography on Mono Q Sepharose or other suitable quaternary ammonium salt based matrix, with elution using a linear sodium chloride gradient (0–1.0 M)in an aqueous buffer containing 1 mM EDTA, 1 mM dithiothreitol, 0.1% taurocholate,0.5% n-octylglucoside, 0.5% CHAPS, 20 mM Tris, pH 7.4; and affinity chromatography using LTC2 affinity chromatography (B. Spur et al., Tetrahedron Lett. 24, 2135–2136 (1983) discloses an $LTC_2$-linker-biotin-streptavidin-agarose affinity chromatography matrix), with elution using a linear co-gradient of sodium chloride (0–1.0 M) and reduced glutathione (0–4 mM) in an aqueous buffer which is essentially the same as the elution buffer used in the anion exchange chromatography step, except without reduced glutathione. A method for the purification of human leukotriene $C_4$ synthase from THP-1 cells (human monocytic leukemia cell line) which utilizes anion exchange chromatography, $LTC_2$ affinity chromatography and gel permeation chromatography is disclosed in D. W. Nicholson, et al., PNAS (USA) 90, 2015–2019 (1993).

In another of its aspects, the present invention entails antisense nucleic acids or antisense oligonucleotides (or oligonucleotide analogs) which are about 12 to about 30 nucleotides in length and which have a sequence corresponding to a segment of the nucleic acid sequence represented by Seq. ID No. 3 (excluding the 5'- terminal and 3'-terminal restriction endonuclease sites). In this embodiment of the present invention, such antisense nucleic acids are capable of hybridizing with $LTC_4$-encoding mRNAs and preventing translation of the mRNA into $LTC_4$ synthase or a polypeptide fragment thereof having $LTC_4$ synthase activity. Preferably, an antisense oligonucleotide or oligonucleotide analog corresponds to a segment of the nucleic acid sequence which is in the region from about nucleotide 350 to about nucleotide 679, more preferably from about nucleotide 450 to about nucleotide 624, and most preferably from about nucleotide 500 to about nucleotide 599 of Seq. ID No. 3.

Antisense oligonucleotides and oligonucleotide analogs of the present invention are useful pharmaceutical agents in the treatment of $LTC_4$- and $LTD_4$-mediated conditions, including, but not limited to chronic asthma. Antisense oligonucleotides which are non-ionic oligonucleotide analogs are presently preferred because they generally have increased resistance to nuclease digestion (i.e., have a longer half-life) and are capable of crossing the cell membrane of a viable cell. Non-ionic nucleoside analogs and methods for making oligonucleotides with nuclease resistant bonds (i.e., analogs of phosphodiester bonds) include nucleoside alkylphosphonate and nucleoside arylphosphonate analog (U.S. Pat. Nos. 4,511,713 and 4,469,863); phosphorothioate and phosphorodithioate nucleosides (U.S. Pat. Nos. 5,151,510 and 5,292,875) and phosphoroselenoate nucleosides (Brill et al., *J. Am. Chem. Soc.,* 111, 23–21 (1989)). Non-ionic oligonucleotide analogs advantageously are capable of diffusing across the cell membrane of a viable cell. Once inside the cell, antisense oligonucleotides and analogs thereof are capable of hybridizing with $LTC_4$ synthase encoding mRNA and preventing production of $LTC_4$ synthase, thus antisense oligonucleotides and oligonucleotide analogs of the present invention are $LTC_4$ synthase "inhibitors" which inhibit the production of $LTC_4$ synthase.

Therapeutically effective antisense oligonucleotides and oligonucleotide analogs of the invention may be selected based on their ability to inhibit the cellular production of $LTC_4$ synthase. Conveniently, in vitro inhibition assays may be carried out using viable cells which express endogenous or recombinant $LTC_4$ synthase, including THP-1 cells and transformed host cells of the invention which harbor an $LTC_4$ synthase encoding DNA. A suitable assay entails culturing such cells in the presence and absence of at least one antisense oligonucleotide analog of the invention for a sufficient amount of time for the antisense oligonucleotide analog to enter the cells and hybridize with $LTC_4$ synthase mRNA and affect $LTC_4$ synthase expression. For example, cells may be cultured in the presence of (test cells) or absence of (negative control cells) antisense oligonucleotide analogs of the invention for several hours to several days or more in order to observe inhibition of production of $LTC_4$ synthase. Negative control cells may receive either no exogenously added oligonucleotide or an oligonucleotide having a sequence which is not antisense (e.g., a random sequence) with respect to $LTC_4$ encoding mRNAs. Oligonucleotide analogs may be added at one or more effective concentrations (e.g., from about 0.1 micromolar to about 10 millimolar) and optionally may be replenished regularly (e.g., daily) for the duration of the incubation.

Whether and to what extent cellular production of $LTC_4$ synthase is inhibited by antisense oligonucleotides is determined by comparing the amount of $LTC_4$ synthase activity present in the test cells, relative to the amount of $LTC_4$ synthase activity observed in cells not treated with an antisense oligonucleotide of the invention. After the cells have been cultured in the presence or absense of antisense oligonucleotides for a predetermined amount of time, measurement of the effectiveness of inhibition may be carried out by determining the amount of $LTC_4$ synthase activity associated with the cells by adding a substrate effective amount of $LTA_4$, and reduced glutathione, if necessary, and detecting the production of $LTC_4$. Reduced glutathione is a necessary substrate which is provided endogenously by viable cells (i.e., when whole cells are the source of $LTC_4$ synthase activity); reduced glutathione is added exogenously when the assay is carried out using a microsomal preparation or an $LTC_4$ synthase containing solution as the source of enzymatic activity. Preferred methods for measuring $LTC_4$ synthase activity are described hereinbelow and in Example 4.

The antisense oligonucleotides and antisense oligonucleotide analogs of the present invention can be used in the treatment of diseases which are characterized by elevated levels of $LTC_4$, $LTD_4$ and/or $LTE_4$, such as chronic asthma and allergic rhinitis.

The antisense oligonucleotide analogs of the present invention can be formulated into suitable pharmaceutical compositions according to known methods for preparing pharmaceutical compositions. The antisense oligonucleotide analogs can be combined in admixture with pharmaceutically acceptable diluents, excipients or carriers (hereinafter referred to collectively as "carrier" materials) suitably selected with respect to the intended form of administration, including oral tablets, capsules, soft gels, elixirs and the like.

For example, for oral administration in the form of tablets or capsules, a therapeutically effective amount of one or more antisense oligonucleotide analogs of the present invention may be combined with one or more pharmaceutically acceptable carriers, such as lactose, starch, sucrose, magnesium stearate, mannitol, and the like. It also may be desirable to include suitable binders, lubricants, disintegrating agents and coloring agents. Suitable binders include starch, gelatin, natural sugars, corn sweeteners, natural and synthetic gums, such as sodium alginate, carboxymethylcellulose, polyethylene glycol, acacia, waxes and the like. Lubricants for use in these dosage forms include boric acid, sodium benzoate, sodium acetate, sodium chloride, magnesium stearate and the like. Suitable disintegrating agents include starch, methyl cellulose, agar, bentonite, guar gum and the like.

For intravascular, intraperitoneal, subcutaneous or intramuscular administration, or for administration by inhalation, i.e., aerosols, one or more of the antisense oligonucleotides (analogs) of the present invention can be combined with a suitable carrier, such as water, saline, aqueous dextrose and the like. Administration by inhalation in an aerosol form is presently preferred because it can deliver compositions of the present invention rapidly into the bronchi. Methods for formulating pharmaceutical compositions for various routes of administration are described in Remington's Pharmaceutical Sciences, 17 Ed., (1985) Mack Pub. Co. edited by A. Gennaro et al.

Regardless of the route of administration selected, a therapeutically effective quantity of one or more antisense compounds of the invention may be employed in the treatment of an inflammatory disease characterized by elevated levels of $LTC_4$, $LTD_4$ and $LTE_4$. The dosage regimen for preventing or treating such inflammatory conditions with compounds of the present invention may be selected in accordance with a variety of factors, including the type, age, weight, sex and medical condition of the patient. The severity of the inflammatory condition, the route of administration and the particular compound employed in the treatment. A physician or veterinarian of ordinary skill can readily determine and prescribe an effective amount of an antisense oligonucleotide (analog) to treat the symptoms of the condition. Relatively low doses could be employed at first and sequentially increased until a maximum response is obtained. Daily dosages of the antisense oligonucleotide analog compounds of the invention are ordinarily in the range of from about 0.2 micrograms per kilogram of body weight up to about 20 milligrams per kilogram of body weight.

In a further of its aspects, the invention involves an in vitro assay for detecting an $LTC_4$ synthase inhibitor compound which method entails combining recombinant human $LTC_4$ synthase and a putative $LTC_4$ synthase inhibitor compound and determining the amount of $LTC_4$ synthase activity relative to a substantially identical amount of recombinant $LTC_4$ synthase but in the absence of any inhibitor compound. The in vitro $LTC_4$ synthase inhibitor assays may be conveniently carried out in a suitable multiwell container such as a microtiter plate. A presently preferred source of recombinant human $LTC_4$ synthase that which is produced by insect cells transfected with a DNA of the invention which is a baculovirus expression vector. Insect cells harboring such DNAs of the invention are capable of expressing elevated levels of recombinant human $LTC_4$ synthase activity.

In an in vitro assay of the invention, the source of $LTC_4$ synthase activity may be either whole, intact recombinant cells, a microsomal membrane preparation or extract, or an aqueous solution of $LTC_4$ synthase. Where whole, intact cells are utilized, they may be added directly to the reaction wells after briefly wahing them in e.g., the assay buffer being used in the assay.

A microsomal fraction from recombinant cells of the invention may be prepared for use in an assay of the present invention by lysing the cells, e.g., by sonication, and subjecting the cellular suspension to differential centrifugation, e.g. 10,000×G, to remove large cellular components, followed by centrifugation at about 100,000×G, to pellet the microsomes. The microsomes may be simply recovered in a suitable assay buffer such as described in Example 4 or may be solubilized in a suitable detergent, such as 2% taurocholate. Other suitable detergent solutions which do not adversely affect $LTC_4$ synthase activity are mentioned in D. W. Nicholson et al., *Eur. J. Biochem.* 209, 725–734 (1992).

An important advantage of using whole, intact cells as the $LTC_4$ synthase source is that it is possible to assess the ability of a putative inhibitor to cross the cell membrane. On the other hand, using a microsomal preparation or $LTC_4$ synthase containing solution eliminates as a variable in the assay the rates which $LTA_4$ and $LTC_4$ cross the cell membrane. It is presently preferred to test the ability of putative inhibitor compounds to inhibit $LTC_4$ synthase activity from whole cells as well as from $LTC_4$ synthase in solution or a solubilized or nonsolubilized microsomal preparation.

As the person of ordinary skill in the art will appreciate, the amount of $LTC_4$ synthase used in each assay may vary widely so long as it is sufficient to produce a detectable signal (i.e., a detectable amount of $LTC_4$) within a suitable time period. It is routine to determine appropriate enzyme and substrate levels in enzymatic assays. The number of cells or amount of protein which is added to each well to provide an appropriate amount of $LTC_4$ synthase activity may be readily determined by titration. In general, an $LTC_4$ assay, in the absence of inhibitor, should be linear with respect to the level of $LTC_4$ synthase activity. It is presently preferred to use a limiting (i.e., non-saturating) amount of $LTA_4$ substrate and a non-limiting (i.e., saturating) amount of reduced glutathione in order to select putative inhibitors which bind to the $LTA_4$ binding site and not the glutathione binding site of $LTC_4$ synthase. A putative $LTC_4$ synthase inhibitor may be tested at one or more concentrations. The putative inhibitor compound is added to one or more wells containing a source of recombinant human $LTC_4$ synthase and allowed to incubate for about 15 minutes or longer, at a temperature between about 4° C.–37° C. to permit binding, if any, of the putative inhibitor compound. Then the temperature of the wells is adjusted to the temperature at which the assay is to be carried out and suitable amounts of substrate, $LTA_4$ and reduced glutathione, are added to start the assay. The conditions for carrying out the assay may vary, but generally the reaction temperature is in the range of from about 15° C. to about 37° C., preferably about 22° C.–27° C. and the reaction time is about 15–60 minutes, preferably about 30 minutes. Where intact cells are used as the source of $LTC_4$ synthase activity, the reaction is then stopped by pelleting the cells and removing the supernatant for analysis of $LTC_4$. Where a microsomal preparation or purified protein preparation is used, the assay is allowed to proceed to substrate exhaustion and then analyzed for $LTC_4$. Detection of $LTC_4$ is well known in the art. A presently preferred means for measuring $LTC_4$ levels is by an enzyme linked immunoassay as well known in the art. An $LTC_4$ ELISA kit which is commercially available from Cayman Chemical Co., Inc. (Ann Arbor, Mich. 48105) is convenient. The level of $LTC_4$ in the well(s) which contain a putative inhibitor compound are compared to the level of $LTC_4$ in the well(s) to which no inhibitor compound was added to determine the efficacy of the putative inhibitor compound.

The following examples describe and illustrate the present invention in more detail.

All of the patents and publications referred to herein are hereby incorporated by reference into this document.

EXAMPLE 1

Isolation of Human $LTC_4$ Synthase Gene

A. Isolation of $LTC_4$ synthase mRNA

Human monocytic leukemia THP1 cells (ATCC # TIB202) were cultured in sterile RPMI-1640 medium (supplemented with 0.2%(w/v) $NaHCO_3$ and 0.03% (w/v) L-glutamine) containing 10% fetal bovine serum. All cultures were grown at 37° C. in a humidified atmosphere containing 6% $CO_2$ in either stationary culture flasks (175 $cm^2$) or spinner flasks (25 rpm). Stock cells were mainitained by subculturing cells every three or four days (or sooner, if cell density exceeded $1.5 \times 10^6$ cells/ ml) in fresh medium at a seed demsity of $10^5$ cells/ml.

THP-1 cells grown as indicated were pelleted by centrifugation at 1000×G. Approximately 2 mls of packed cells were solubilized in 30 mls of Guanidine Isothiocyanate Solution (4 M Guanidine Isothiocyanate, 50 mM Tris HCl pH 7.5, 25 mM EDTA, 100 mM Beta Mercaptoethanol) and homogenized by trituration. 3 mls of 2 M Sodium Acetate pH 4 were added and the solution mixed. 30 mls of water saturated phenol, unadjusted for pH were added and the solution mixed. 30 mls of chloroform were added and the solution shaken vigorously for 10 seconds and placed on ice for 15 minutes with shaking every 5 minutes. The solution was centrifuged for 20 minutes at 10,000×G. The aqueous phase was recovered, combined with one volume of isopropanol, and placed at −20° C. overnight. The solution was centrifuged at 16,000×G for 20 minutes at 4° C. The supernatant was discarded and the RNA pellet solubilized in 15 mls of the Guanidine solution. The RNA was precipitated with one volume of isopropanol at −20° C. overnight. The solution was centrifuged as before. The supernatant was discarded and the pellet solubilized in 10 mls of water at 70° C. for 5 minutes. One-tenth volume of 3 M sodium acetate pH 5.2 was added to the solution and mixed. 2 volumes of ethanol were added, the solution mixed and the RNA precipitated at −20° C. overnight. The solution was centrifuged at 16,000×G for 10 minutes at 4° C. The supernatant was discarded and the RNA pellet solubilized in 3.5 mls water at 70° C. for 5 minutes. The RNA was precipitated with sodium acetate and ethanol as before. The RNA was centrifuged at 16,000×G for 10 minutes at 4° C. The supernatant was discarded and the pellet solubilized in 2 mls of water. It was precipitated with sodium acetate and ethanol as before. The RNA was centrifuged as before and the pellet solubilized in 2 mls of water. A 1:100 dilution was prepared with 3 μl of the RNA solution and the absorbance taken at 260 nanometers. The quantity of RNA was determined to be 8 mg by the following formula: $OD_{260}$×Dilution×40×Volume in mls=# of micrograms of RNA. The RNA was precipitated with sodium acetate and ethanol as before.

B. Poly A Selection 4 mls of the RNA, water, sodium acetate, ethanol solution were centrifuged at 16,000×G for 10 minutes at 4° C. The supernatant was discarded and the pellet dried under a vacuum. The dried RNA pellet was suspended in 5 mls elution buffer (10 mM Tris HCl pH 7.5, 1 mM EDTA). Approximately 1 gram of oligo dT cellulose (Collaborative Research, Type 3) was slurried in elution buffer and transferred to a small disposable sterile column and allowed to drain. Three bed volumes of 0.1 N sodium hydroxide were applied to the column and drained through it. 10 bed volumes of binding buffer (elution buffer with 500 mM sodium chloride) were applied to the column and allowed to drain through. The pH of the eluent was checked to verify that the pH had returned to approximately 7.5. The RNA was placed at 70° C. for 5 minutes, chilled on ice and adjusted to 500 mM NaCl with one-tenth volume of 5 M NaCl. The RNA was passed through the column. The column was washed with 10 bed volumes of binding buffer. The A+ RNA was eluted with 2 bed volumes of elution buffer followed by one bed volume of elution buffer. The eluents were pooled and precipitated with one-tenth volume of 3 M sodium acetate pH 5.2, and 2 volumes of ethanol overnight at −20° C. The A+ RNA was centrifuged at 16,000×G for 10 minutes at 4° C. The supernatant was discarded and the pellet dried under vacuum. The A+ RNA was dissolved in 400 μl of water and the absorbance taken as described in the previous section. The concentration of A+ RNA was determined to be 0.7 μg per μl. The A+ RNA was dispensed into 50 μl aliquots and stored at −80° C.

C. Reverse Transcriptase—Polymerase Chain Reaction (RT-PCR)

1 μg of THP1 A+ RNA and 5 μg of Random Primers (Invitrogen) were combined in a final volume of 20 μl of water. The RNA/Primer solution was heated at 65° C. for 10 minutes followed by chilling on ice for 2 minutes. Reverse transcription was in a 50 μl volume containing the RNA/Primer solution, 50 mM Tris HCl pH 8.3, 75 mM KCl, 3 mM $MgCl_2$, 1 mM DTT, 0.5 mM each dNTP, 1000 units of Superscript II (BRL), and 10 units of placental RNAse inhibitor (Invitrogen) at 42° C. for 90 minutes. 5 μl of the reverse transcription reaction was subjected to PCR under mineral oil in a 50 μl reaction volume containing 10 mM Tris HCl pH 8.3, 50 mM KCl, 1.5 mM $MgCl_2$, 0.001% gelatin, 0.25 mM each dNTP, 50 picomoles of each primer, and 2.5 units of Amplitaq (Perkin Elmer, Norwalk, Conn.; Catalog #N808-0070) with 30 cycles of 94° C. for 30 seconds, 42° C. for 60 seconds, 72° C. for 30 seconds. The primers used were IC42F (5'-ATGAAIGATGAIGTIGCICTICTIGC-3'; SEQ ID No.4) and IC43R (5'-ACICGGAAIGCIATICGIGC-3'; SEQ ID No. 5). 10 μl of the RT-PCR reaction was run on an agarose gel that was 2% low melt and 1% high melt in 1X TAE (40 mM Tris Acetate, 1 mM EDTA) with 0.3 μg per ml Ethidium Bromide. A band of approximately 105 base pairs was visualized under UV light, cut from the gel with a scalpel and purified by Qiaex (Qiagen). The agarose was solubilized in 500 μl of Qiaex buffer QX1 in the presence of 5 μl of Qiaex bead suspension for 10 minutes at 50° C. with vortexing every 2 minutes. The solubilized agarose solution was spun in a microfuge at full speed for 30 seconds. The supernatant was discarded and the pellet suspended in 500 μl of Qiagex buffer QX2. The solution was centrifuged in a microfuge at maximum speed for 30 seconds and the supernatant was discarded. The wash in buffer QX2 was repeated. The pellet was washed similarly with 500 μl Qiagen buffer QX3 two times. The pellet was centrifuged again for 30 seconds at maximum speed and the residual supernatant was discarded. The pellet was dried under a gentle stream of nitrogen for about 5 seconds until the pellet had just dried. The pellet was suspended in 10 μl of water and incubated at 50° C. for 10 minutes with vortexing every 2 minutes. The suspension was centrifuged for 30 seconds at maximum speed in a microfuge, the supernatant recovered and chilled on ice.

D. TA Cloning

5 μl of the gel purified, 105 base pair DNA fragment was ligated into pCR II (Invitrogen #K2000-01 version 1.3). 50 ng of the vector pCR II were combined with 1 μl of 10X ligation buffer, 5 μl of the gel purified DNA fragment, and 1 μl of T4 DNA Ligase. The reaction was incubated overnight at 12° C. INVαF' frozen competent *E. coli* cells were transformed with the ligation mix as recommended by Invitrogen. 2 μl of 500 mM Beta-mercaptoethanol was combined with one vial of INVαF' frozen competent *E. coli* cells and mixed by tapping the tube. 1 μl of the ligation was added to the cells and mixed by gentle tapping of the tube. The mixture was incubated on ice for 30 minutes. The tube was placed at 42° C. for 45 seconds. The tube was placed on ice for 2 minutes. 450 μl of room temperature SOC media (2% Bacto Tryptone, 0.5% Bacto Yeast Extract, 10 mM NaCl, 2.5 mM KCl, 10 mM $MgCl_2$, 10 mM $MgSO_4$, 20 mM Glucose) was added to the tube and the mixture was incubated for 60 minutes at 37° C. in a gyratoty shaker at 225 rpm. 25 μl of 40 mg/ml X-Gal was spread onto an LB amp plate (LB is 1% Bacto Tryptone, 0.5% Bacto Yeast Extract, 1% NaCl and an LB amp plate is LB with 1.5% Agar and 10 μg per ml ampicillin.) and allowed to soak into the plate for 60 minutes. The transformed cells were placed on ice. 25 μl of the transformed cells were spread onto the plate and incubated at 37° C. overnight. The plate had 1 blue, 2 white, and 2 intermediate colonies. All 5 were picked and used to inoculate 3 mls LB amp each (LB with 10 μg per ml ampicillin). The cultures were grown overnight in a rotating wheel at 37° C. 100 μl, of each culture was removed and stored at 4° C. The remaining cultures were centrifuged at 5,000×G for 5 minutes at 4° C. The supernatants were discarded and plasmid DNA was isolated from the pellets using a Magic Mini Prep kit (Promega, Madison, Wis.; Catalog #A7100). The cell pellets were suspended in 200 μl of 50 mM Tris HCl, pH 7.5, 10 mM EDTA. 200 μl of 0.2 N NaOH was added and the tubes shaken to mix. 200 μl of 2.55 M Potassium Acetate pH 4.8 was added and the tubes shaken to mix. The tubes were spun in a microfuge at full speed for 5 minutes. The supernatants were recovered. 1 ml of Promega Magic Resin was added to the supernatants and mixed. The mixtures were pulled into Promega Magic Mini Columns by vacuum. The columns were washed with 2 mls of 100 mM NaCl, 10 mM Tris HCl pH 7.5, 2.5 mM EDTA, 50% ethanol which was pulled through the columns by vacuum. The columns were placed in microfuge tubes and spun in a microfuge at maximum speed for 30 seconds. The columns were transferred to new tubes and 50 μl of water was added to the columns. The columns were allowed to sit at room temperature for 60 seconds followed by centrifugation in a microfuge for 30 seconds at maximum speed. The eluates were recovered as plasmid mini prep DNA. 5 μl of the plasmid mini prep DNAs were digested with the restriction endonuclease Eco R1 (20 units) in 100 mM NaCl, 50 mM Tris HCl pH 7.5, 10 mM MgCl₂, 1 mM DTT at 37° C. for 1 hour. The digests were electrophoresed on a 2% low melt 1% high melt agarose gel in 1X TAE with 0.3 μg per ml Ethidium Bromide. When visualized under UV light, 4 of the 5 digests showed a band that migrated slightly slower than a reference band of 118 base pairs. The expected size of a 105 base pair insert in pCRII would be 125 base pairs if the insert was cut out with Eco R1.

E. Sequencing

The plasmid mini preps that had the 105 base pair inserts were sequenced with the Cyclist DNA Sequencing Kit from stratagene. In a 30 μl volume, 10 μl of the plasmid mini prep DNA was combined with 4 μl of 10X sequencing buffer, 20 picomoles of the universal primers M13F or M13R, 10 μCi of [$\alpha^{33}$P] dATP, and 2 units of Taq DNA polymerase. 6.5 μl of the reactions were aliquoted to each of 4 tubes containing 3 μl of either 600 μM ddATP, 600 μM ddCTP, 100 μM ddGTP, or 1000 μM ddTTP. One drop of mineral oil was placed on top of the reactions and the tubes were placed in a thermal cycler. The reactions were heated to 95° C. for 5 minutes followed by 30 cycles of 95° C. for 30 seconds, 60° C. for 30 seconds, 72° C. for 60 seconds. After cycling, the tubes were chilled on ice and 5 μl of stop solution was added to each tube. 3 μl of each reaction were electrophoresed on a standard 8% polyacrylamide sequencing gel containing 7 M urea in 1X TBE (89 mM Tris Borate, 89 mM Boric Acid, 2 mM EDTA) at 70 watts constant power until the Bromophenol Blue dye was a few cm from the bottom of the gel. The gel was fixed in 10% acetic acid for 30 minutes and dried under a vacuum at 80° C. for 30 minutes. The dried gel was placed next to X ray film overnight at room temperature. The autoradiogram was read and and yielded the following sequence:
5'-ATGAAGGATGAGGTGGCGCTGCTGGCTGCTGT-CACCCTCCTGGGAGTCCTGCTGCAAGCC TACTTCTCCCTGCAGGTGATCTCGGCCCGCATCGC-CTTCCGCGTA-3'; SEQ ID No. 6, from clone 4, which was named pMON23957. This cDNA codes for the amino acid sequence published previously for the amino terminus of Leukotriene C4 Synthase. The deduced amino acid sequence from this cDNA differs from the published sequence at amino acid position 21 where a glycine is reported and this cDNA codes for a tyrosine. 9 other clones were obtained from a re-plating of the ligation described in Example 1 D, above, and sequenced. All of the clones code for a tyrosine at amino acid position 21. Three oligonucleotides were designed based on the sequence that was not derived from the primers used in RT-PCR. That sequence is nucleotides 27 through 84. Those primers are CLC41R (5'-CGAGATCACCTGCAGGGAGAAGTAGGCT-TGCAGCAGGACTCCCAGGAGGGTGACA GCA-3'; SEQ ID No. 7) CLC42R (5'-TGCAGCAGGACTCCCAGGAGGGTGACAGCA-3'; SEQ ID No.8) and CLC43R (5'-CGAGATCACCTGCAGGGAGAAGTAGGCTTG-3'; SEQ ID No. 9).

F. cDNA Library Construction

A cDNA library had been previously constructed from THP1 A+ RNA that had been isolated and A+ selected as described in this document. The cDNA library was constructed with a kit from Stratagene (catalog #200400). 5 μl of 10 first strand buffer were placed in a microfuge tube. The following reagents were added in order: 5 μl of 100 mM DTT, 3 μl first strand methyl nucleotide mixture, 2 μl linker-primer (2.8 μg), water to bring the volume to 39.5 μl, unit of RNAse block II, and 5 μg of THP1 A+ RNA. The tube was incubated at room temperature for 10 minutes. 2.5 μl of M-MLV reverse transcriptase was added (final volume of the reaction was 50 μl). 5 μl was removed to a separate tube containing 0.5 μl of [$\alpha^{32}$P] dATP and both tubes were incubated at 37° C. for 60 minutes. The 45 μl remaining non-radioactive first strand reaction was placed on ice and had the following reagents added in order: 40 μl 10X second strand buffer, 15 μl 100 mM DTT, 6 μl mM second strand nucleotide mixture, 278.5 μl water, 2 μl [$\alpha^{32}$P] dATP. The reaction was mixed and 4.5 μl RNAse H (4 units per μl) and 11.2 μl DNA polymerase I (10 units per μl) were added and the reaction mixed. The reaction was incubated at 16° C. for 2.5 hours. The reaction was chilled on ice. One-half volume of TE saturated phenol (phenol repeatedly mixed with TE(10 mM Tris, 1 mM EDTA) until the pH of the TE after phase separation stabilizes) was added to the reaction and one-half volume of chloroform was added to the reaction. The tube was vortexed and centrifuged for 2 minutes in a microfuge at maximum speed. The aqueous phase was recovered and an equal volume of chloroform was added to it. The tube was vortexed and centrifuged as before. The aqueous phase was recovered. 33.3 μl of 3 M sodium acetate and 867 μl of ethanol were added to the tube. The DNA was precipitated overnight at −20° C. The tube was placed in a microfuge and centrifuged for 60 minutes at maximum speed at 4° C. The supernatant was discarded and 1 ml of 80% ethanol was gently added to the tube. The tube was centrifuged for 2 minutes at maximum speed in a microfuge. The supernatant was discarded and the DNA pellet dried under a vacuum. The DNA was suspended in 43.5 μl of water at room temperature for 15 minutes. 4.5 μl were removed and stored for later analysis. To the remainder was added; 5 μl 10×T4 polymerase buffer, 2.5 μl 2.5 mM dNTP mixture, and 3 μl T4 DNA polymerase (2.9 units per μl). The reaction was gently mixed and incubated at 37° C. for 30 minutes. 50 μl water were added and the reaction phenol chloroform extracted as described previously. The DNA was precipitated with 7 μl 3 M sodium acetate and 226 μl ethanol overnight at −20° C. The DNA was centrifuged for 60 minutes and washed with 150 μl of 80% ethanol as described above. The pellet was dried under a vacuum. The pellet was suspended in 7 μl of EcoRI adaptors. 1 μl 10×ligase buffer, 1 μl 10 mM rATP, and 1 μl T4 DNA ligase (4 Weiss units per μl) were added to the tube, mixed and incubated at 8° C. overnight. The ligation was placed at 70° C. for 30 minutes then room temperature for 5 minutes. 1 μl 10X ligase buffer, 2 μl 10 mM rATP, 6 μl water, and 1 μl T4 polynucleotide kinase were added. The reaction was incubated at 37° C. for 30 minutes, followed by 70° C. for 30 minutes. The reaction was kept at room temperature for 5 minutes. 28 μl of Xho I buffer suppliment and 3 μl Xho I (40 units per μl) were added and the reaction incubated at 37° C. for 90 minutes. A sephacryl S-400 column was constructed in a 1 ml plastic syringe by plugging the end with cotton, filling it with sephacryl S-400, spinning it at 600×G for 2 minutes, filling it with more sephacryl S-400, respinning as before, adding 300 μl 1×STE, spinning as before, adding 300 μl 1×STE and spinning as before. 5 μl of 10×STE were added to the Xho I digest and it was applied to the top of the column. The column was spun as before. 60 μl of 1×STE was applied to the column and the column was spun as before. The addition of 60 μl 1×STE was repeated. The combined eluents were phenol chloroform extracted as before. The DNA was precipitated with ⅒ volume of 3 M sodium acetate and 2 volumes of ethanol at −20° C. overnight. The DNA was centrifuged at maximum speed in a microfuge at 4° C. for 60 minutes. The supernatant was discarded and the pellet washed with 150 μl 80% ethanol as before. The cDNA was dried under a vacuum and dissolved in 10 μl water. 2.5 μl of the cDNA was combined with 0.5 μl 10×ligation buffer, 0.5 μl 10 mM rATP, 1 μl Uni-Zap XR (1 μg per μl) and 0.5 μl T4 DNA ligase (4 Weiss units per μl) and mixed. The reaction was incubated at 12° C. overnight. The cDNA was packaged with a lambda packaging kit (Stratagene, La Jolla Calif.; Catalog #200214) by combining 4 μl of the ligation with a just thawed freeze/thaw extract and quickly adding 15 μl of a just thawed sonic extract and gently mixing. The packaging reaction was incubated at room temperature for 2 hours. 500 μl of SM (5.8 g/liter NaCl, 2 g/liter $MgSO_4$, 25 mls/liter 2 M Tris HCl pH 7.5, 5 mls 2% gelatin/liter) were added to the packaging reaction followed by 20 μl chloroform and gently mixed. SURE cells (Stratagene, La Jolla, Calif., Catalog #200294) were grown overnight in LB with 0.2% maltose, 10 mM $MgSO_4$ then centrifuged at 5,000×G for 5 minutes. The cells were suspended in one-half volume of 10 mM $MgSO_4$. Serial dilutions of the packaged library were prepared in SM. 10 μl of these were combined with 200 μl of SURE cells. These were incubated at 37° C. for 15 minutes gently shaken. 3 mls of NZY top agar (NZY is 5 g/liter NaCl, 1 g/liter $MgSO_4$, 5 g/liter yeast extract, 10 g/liter NZ amine adjusted to pH 7.5. NZY top agar is NZY broth with 0.7% agar) at 50° C., 15 μl of 500 mNM IPTG and 50 μl of 250 mg/ml X-Gal were added to the tubes, which were swirled and poured onto 100 mm NZY plates (NZY with 1.5% agar). The plates were allowed to cool for 10 minutes and incubated overnight at 37° C. The $10^{-4}$ plate had approximately 100 clear plaques indicating that the library titer was $5\times10^5$ pfu total. The library was stored at 4° C. for about 11 months. The library was re-titered and found to contain $1.7\times10^5$ pfu total. 2.5 μl of the cDNA left over from the cDNA construction were ligated into Uni-Zap XR as before. The ligation was packaged and titered. The titer was $2\times10^5$ pfu total.

G. cDNA Library Screening

Both packaged libraries were combined and plated for screening. XL1 Blue cells (Stratagene, La Jolla, Calif.; Catalog #200268) were grown overnight and suspended in 10 mM $MgSO_4$ as the SURE cells were. 0.6 mls of the XL1 Blue cells were combined with 1/10 of the combined, packaged libraries in each of 10 tubes. These were incubated gently shaken at 37° C. for 15 minutes. 8 mls of NZ top agarose (NZY without the yeast extract and with 0.7% agarose) were added to each of the tubes, swirled and poured onto each of 10, 150 mm NZY plates. The plates were incubated at 37° C. for 8 hours and stored at 4° C. overnight. Nitrocellulose filters were placed on the plates for 1 minute and marked for orientation. This was repeated 3 more times with the time in contact with the plaques was increased by 30 seconds with each succesive filter. These were placed in 0.5 N NaOH, 10X SSPE (87 g/liter NaCl, 13.8 g/liter $NaH_2PO_4 \bullet H_2O$, 3.7 g/liter EDTA, pH 7.4) for one minute, 10X SSPE for one minute, 1 M Tris HCl pH 7.5, 10 X SSPE for one minute. The filters were baked at 80° C. under vacuum for 2 hours. The filters were washed in 5X SSPE at 42° C. for 2 hours. The filters were pre-hybed in 20% formamide, 5X SSPE, 5X Denharts (50X Denharts is 10 g/liter each; ficoll, polyvinylpyrrolidone, and BSA Pentax fraction V), 100 μg per ml freshly boiled sheared salmon sperm DNA, 0.1% SDS overnight at 42° C. shaken gently. The oligonucleotides CLC41R, CLC42R and CLC43R were kinased for probes. 150 μCi of $[\lambda^{32}P]$ rATP was dried under vacuum for each of the three oligos. Each was suspended in 3 μl water that contained one of the oligos at 20 picomoles per μl. 1 μl 5×Kinase buffer (250 mM Tris HCl pH 7.5, 50 MM $MgCl_2$, 25 mM DTT, 0.5 mM EDTA, 0.5 mM spermidine was added to each, 1 μl (10 units) T4 Polynucleotide kinase was added to each. The reactions were incubated at 37° C. for 45 minutes. 1 μl of 10 mg/ml tRNA and 45 μl of water were added to each tube. Biorad P-6 columns were prepared by allowing the buffer to drain, spinning in a clinical centrifuge on setting 6 for 2 minutes, and discarding the buffer. The kinase reactions were placed on the prepared columns and spun in a clinical centrifuge on setting 6 for 4 minutes. 1 μl of each was counted in a scintillation counter. Fresh pre-hybe solution was prepared and two filters from each plate were hybridized with either $1\times10^6$ cpm per ml CLC41R or $1\times10^6$ cpm per ml each CLC42R and CLC43R overnight at 42° C. with gentle agitation. The filters were washed two times for 15 minutes each time in 5X SSPE, 0.1% SDS at 42° C. followed by two times for 15 minutes each time in 1X SSPE, 0.1% SDS at 42° C. The filters were used to expose X Ray film at −80° C. with intensifying screens for 4 days. The autoradiograms were developed and lined up with the phage plates. Three quadruplicating spots on the autoradiograms were used to select three areas on the plates to remove plaques. The large end of pasteur pipettes were pushed through the plates and the plug expelled into 1 ml SM with 50 μl chloroform. The phage stocks were stored at 4° C. overnight. XL1 Blue cells were prepared as described previously. 200 μl of cells were combined with $10^{-3}$ or $10^{-4}$ dilutions of the phage stocks. These were incubated at 37° C. for 15 minutes with gentle agitation and plated onto 100 mm NZY plates in 3 mls of NZ top agarose. The plates were incubated for 8 hours at 37° C. and stored overnight at 4° C. Nitrocellulose filters were used to lift plaques as before. The filters were denatured, baked, washed, pre-hybed, hybed and washed as before except 2 lifts were done for each plate and all 3 oligos were used together. The lifts were exposed to film as before except for three days instead of four. Two isolated positive plaques were cored from one of the two dilutions from each set of plates (six (6) total phage stocks). The cores were done with the small end of a pasteur pipette and placed in 500 μl of SM with 20 μl of chloroform. The phage stocks were stored overnight at 4° C.

H. Phagemid Rescues

XL1 Blue cells were grown and prepared as before. 200 μl of the cells were combined with 100 μl of each of the six phage stocks and 1 μl of ExAssist helper phage. The tubes were incubated at 37° C. for 15 minutes with gentle agitation. 3 mls of 2XYT (10 g/liter NaCl, 10 g/liter yeast extract, 16 g/liter Bacto-Tryptone) were added to each of the six tubes and incubated at 37° C. for 2.5 hours with agitation. The tubes were heated to 70° C. for 20 minutes and centrifuged at 4000×G for 15 minutes. The supernatant were recovered and stored at 4° C. 1 μl of the supernatants was combined with 200 μl of SOLR cells (Stratagene, LaJolla Calif.; Catalog I 200298) that were prepared like the XL1 Blue cells. These were incubated at 37° C. with gentle agitation for 15 minutes. 50 μl of each were plated on LB amp plates and incubated overnight at 37° C. Each of the six plates had more than 100 colonies. One was picked from each plate and used to inoculate 3 mls of LB amp each. These were grown overnight and plasmid miniprepped as described previously. 5 μl of each were digested with 20 units each Eco RI and Xho I. These were electrophoresed on a 1% agarose gel as described previously. 5 of the 6 contained inserts of approximately 600 base pairs. One of the clones was sequenced with the M13F universal primer and deduced the N-terminal protein sequence that has been reported for LTC$_4$ Synthase. This clone was named pMON23959 and was completely sequenced.

I. Subcloning

Oligonucleotides were designed to engineer restriction sites onto the open reading frame of pMON 23959. The oligos were: ECOC4F (5'-GATCGAATTCATGAAAGA-CGAAGTTGCTCTGCTGGCTGC-3'; SEQ ID No. 10), BAMC4F (5'-GATCGATGGATCCATGAAGGACGAG-GTAGCTCTACTGGC-3'; SEQ ID No. 11), and EXC4R (5'-GATCGAATTCGGATCCTCAGGCCCACGGCAGC-AGCG-3'; SEQ ID No. 12). PCR reactions were prepared with 20 ng of pMON23959, 40 picomoles of EXC4R, and 40 picomoles of either BAMC4F or ECOC4F. PCR was in 10 mM Tris HCl pH8.3, 50 mM KCl 1.5 mM MgCl$_2$, 0.001% gelatin, 0.25 mM each dNTP, 5% DMSO and 2.5 units of Amplitaq. The reactions were carried out under mineral oil with 30 cycles of 94° C. for 30 seconds, 60° C. for 60 seconds, 72° C. for 30 seconds. 10 μl of each reaction were electrophoresed on 1% agarose in 1X TAE to verify amplification. Bands of approximately 470 base pairs were visualized under UV light from both reactions. The remaining reactions were purified with Promega PCR Clean up Kit. The aqueous phases were transferred to fresh tubes and 100 μl of Direct Purification Buffer were added and mixed. 1 ml of Magic PCR Preps Resin was added to each and mixed. The supensions were placed in 3 ml syringes fitted with Promega Minicolumns. The suspensions were forced into the minicolumns. 2 mls of 80% isopropanol were forced through the minicolumns. The columns were removed from the syringes and placed in microfuge tubes and centrifuged at maximum speed for 30 seconds. The minicolumns were placed in fresh microfuge tubes, and 50 μl of water were added to each column. After 1 minute at room temperature, the columns were centrifuged for 30 seconds at maximum speed in a microfuge and the eluates were recovered and placed on ice. The purified PCR products were adjusted to 100 mM NaCl, 50 mM Tris HCl pH7.5, 10 mM MgCl$_2$, 1 mM DTT. 40 units of either Eco RI or Bam HI were added and the reactions incubated at 37° C. for 60 minutes. The Promega PCR cleanup was repeated on these digests. 5 μl of each were ligated in a 10 μl volume into 100 ng of either Eco RI digested M13 mp19 or Bam HI digested M13 mp19 in 50 mM Tris HCl pH 7.8, 10 mM MgCl$_2$, 10 mM DTT, 1 mM rATP, 25 μg per ml BSA, 6 Weiss units of T4 DNA Ligase at 16° C. overnight. TG1 cells were grown in a 50 ml culture in LB to an OD$_{600nm}$ of 0.5. The cells were centrifuged at 5000×G for 5 minutes at 4° C. The supernatant was discarded and the cells supended in 9 mls of ice cold 50 mM CaCl$_2$, 10 mM NaCl, 25 mM Tris HCl pH 7.5. The cells were incubated on ice for 30 minutes follwed by centrifugation as before. The cells were suspended in 5 mls of fresh ice cold 50 mM CaCl$_2$, 10 mM NaCl, 25 mM Tris HCl pH 7.5. 200 μl of these competent cells were combined with 5 μl of the ligations (seperately) and gently mixed. These transformations were incubated on ice for 30 minutes. The transformations were warmed to 42° C. for 1 minute. 3 mls of LB top agar, 2 μl of 500 mM IPTG, and 25 μl of 4% X-Gal were added to the transformations, swirled and poured onto 100 mm LB plates. The plates were incubated at 37° C. overnight. 6 clear plaques were cored from both the EcoRI ligation and the Bam HI ligation (12 plaques, total) with the small end of a pasteur pipette and put in 5 mls of 2XYT. The cultures were grown for 6 hours agitated at 37° C. The cultures were centrifuged at 16,000×G for 10 minutes. The pellets were stored at −20° C. The supernatants were centrifuged again like before. The second spin supernatants were recovered and combined with 1.25 mls of 20% PEG, 2.5 M NaCl. These were mixed and stored overnight at 4° C. The phage preps were centrifuged at 16,000×G for 10 minutes at 4° C. The pellets were recovered and suspended in 400 μl TE. 400 μl of phenol were added to the tubes, vortexed, and incubated on ice for 15 minutes with occasional vortexing. 400 μl of chloroform were added, the tubes vortexed and centrifuged in a microfuge at maximum speed for 2 minutes. The aqueous phases were recovered and combined with 400 μl of chloroform, vortexed and centrifuged as before. The aqueous phases were precipitated with 1/10 volume of 3 M Sodium acetate and 2 volumes of ethanol overnight at −20° C. The DNAs were centrifuged at maximum speed in a microfuge for 10 minutes at 4° C. The supernatants were discarded and 400 μl of 70% ethanol were added to the tubes. The tubes were centrifuged as before except for only 5 minutes. The supernatants were discarded. The DNA pellets were dried under a vacuum and dissolved in 50 μl of water. Two of these DNAs were completly sequenced and found to contain no differences from pMON 23959 except for the appropriate restriction sites flanking the open reading frame. LTC$_4$ Synthase in M13mp19 as a Bam HI fragment is pMON 23960. LTC$_4$ Synthase in M13mp19 as an Eco RI fragment is pMON 23961.

EXAMPLE 2

Subcloning into Expression Vectors

The Eco RI and Bam HI cDNA fragments from the replicative form DNAs were prepared. The cell pellets that were frozen from the subcloning into M13 were thawed and plasmid mini prep DNA prepared as described before. One half of each plasmid recovered from the mini preps were digested with either Bam HI for transfection of insect cells. (The Eco RI sites alone or in combination with the Bam HI sites may be used to transform or transfect a variety of host cells). The Ban HI-digested plasmids were purified with the Promega PCR cleanup kit as described before. 3 μl of the Bam HI-digested M13 plasmids were used in ligations with approximately 100 ng of Bam HI-digested insect vector pVL 1393 to produce the resulting expression vector which was named pMON 23962. All recombinant plasmids were digested with Pst I to determine that the insert was present and oriented in the expression plasmids correctly.

EXAMPLE 3

Expression of Recombinant Leukotriene C4 Synthase in Insect Cells 5.0 μg of plasmid DNA (pMON 23962) containing the LTC$_4$ synthase gene was mixed with 200 ng of linearized baculovirus DNA (Pharmingen, San Diego, Calif.; Catalog # ) in an eppendorf tube, using the calcium phosphate transfection method described in Summers, M. D., and Smith, G. E. (1987), A manual of methods for baculovirus vectors and insect cell culture procedures, Texas Agriculture Experiment, Station Bulletin no. 1555. To the the same tube, 0.75 ml of transfection 15 buffer (25 mM HEPES, pH 7.1, 140 mM NaCl, 125 mM CaCl$_2$) was added and the tube was vortexed. Sf9 insect cells grown in ITF media [IPL41 media (GIBCO-BRL) plus 10% fetal bovine serum (JRH Biosciences) plus 1X tryptose phosphate broth (GIBCO-BRL)] in a spinner flask were seeded in a 25 cm$^2$ T-flask at 2.0×10$^6$ cells/flask. The cells were allowed to attach for 1 hour at RT (22–27° C.). At the end of 1 hour, the media from the flask was removed and replaced with 0.75 ml of Grace's medium (GIBCO-BRL) containing 10% fetal bovine serum (JRH Biosciences) and 1x antibiotics [Antibiotic-Antimycotic, Cat.# 15240-039 (GIBCO-BRL)]. DNA in the transfection buffer was added dropwise to the the Grace's media (GIBCO-BRL) in the cell culture flask. The flask was incubated at 27° C. for 4 hours in an incubator such that the cells were covered with the liquid in the flask. At the end of 4 hours, the medium from the flask was removed by a pasteur pipette. To the flask was added 5 mls of the ITF media containing antibiotics and the cells were gently washed by rocking the flask. The media was removed and the process repeated two more times. The cells were then incubated at 27° C. in 5 mls of the ITF media containing the antibiotics in the T-flask. After seven days of incubation, the cells were resuspended in the media contained in the flask and transferred to a 15 ml screwcapped tube. The tube containing the cells was spun at 3000 rpm for 10 minutes in a Beckman GPR tabletop centrifuge with the brakes off. The cell-free supernatent was transferred to a new tube and the cell pellet assayed for $LTC_4$ synthase activity.

EXAMPLE 4

Assay Method for Detecting Leukotriene $C_4$ Synthase Activity and Inhibtors Thereof Cells were washed with PBS containing 2 mM $MgCl_2$ and resuspended in same prior to lysis using an Ultrasonics model W-375 ultrasonic processor. Complete cell lysis was accomplished using five 30 second bursts of sonication with 30 second cooling periods between each burst and samples were maintained on ice throughout the procedure.

The Bio-Rad Protein Assay was used to measure the protein concentrations of the cell-free samples as per manufacturers instructions. Bovine serum albumin (Bio-Rad Cat. #500-0007) was used as a relative standard and the diluent used was PBS containing 2 mM $MgCl_2$.

$LTC_4$ synthase activity was measured by the formation of $LTC_4$ from reduced glutathione and $LTA_4$ (free acid) essentially as previously described (Nicholson, D. W., Klemba, M. W., Rasper, D. M., Metters, K. M., Zamboni, R. J., and Ford-Hutchinson, A. W. (1992) Eur. J. Biochem. 209, 725–734). $LTC_4$ levels were determined using an enzyme linked immunoassay kit which is commercially available from Cayman Chemical Co., Ann Arbor, Mich. 48105; catalog #420211). $LTA_4$ methyl ester (1 mg, 3 μmoles) was hydrolyzed under nitrogen using a 30-fold excess of LiOH (100 mM) in dry tetrahydrofuran in a total reaction volume of 1 mL to provide $LTA_4$ in its free acid form. The hydrolysis was incubated overnight in the dark at room temperature. Test samples (100 μL) contained enzyme in 0.1 M potassium phosphate pH 7.4, 0.2 mg/mL L-alpha-phosphatidylcholine, 20 mM $MgCl_2$, and 10 mM reduced glutathione. Reactions were initiated by the addition of an equal volume of 2 μM $LTA_4$ in PBS containing 20 mM $MgCl_2$ and 5 mg/mL bovine serum albumin to the test sample. Assays were incubated for 30 minutes at room temperature with shaking and the $LTC_4$ produced quantitated by EIA.

While the various aspects of the present invention have been described herein with some particularity, those skilled in the art will recognize modifications and variations that remain within the spirit of the invention. These modifications and variations are within the scope of the invention as described and claimed herein.

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 685 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 87..539

(xi) SEQUENCE DESCRIPTION: SEQ ID NO:1:

```
GAATTCGGCA CGAGGAGCAG CAGACGGGGC TAAGCGTTCC CCAGCTCGCC TTCACACACA        60

GCCCGTGCCA CCACACCGAC GGTACC ATG AAG GAC GAG GTA GCT CTA CTG GCT       113
                             Met Lys Asp Glu Val Ala Leu Leu Ala
                              1               5

GCT GTC ACC CTC CTG GGA GTC CTG CTG CAA GCC TAC TTC TCC CTG CAG       161
Ala Val Thr Leu Leu Gly Val Leu Leu Gln Ala Tyr Phe Ser Leu Gln
 10              15                  20                  25

GTG ATC TCG GCG CGC AGG GCC TTC CGC GTG TCG CCG CCG CTC ACC ACC       209
Val Ile Ser Ala Arg Arg Ala Phe Arg Val Ser Pro Pro Leu Thr Thr
             30                  35                  40
```

```
GGC CCA CCC GAG TTC GAG CGC GTC TAC CGA GCC CAG GTG AAC TGC AGC         257
Gly Pro Pro Glu Phe Glu Arg Val Tyr Arg Ala Gln Val Asn Cys Ser
            45                  50                  55

GAG TAC TTC CCG CTG TTC CTC GCC ACG CTC TGG GTC GCC GGC ATC TTC         305
Glu Tyr Phe Pro Leu Phe Leu Ala Thr Leu Trp Val Ala Gly Ile Phe
                60                  65                  70

TTT CAT GAA GGG GCG GCG GCC CTG TGC GGC CTG GTC TAC CTG TTC GCG         353
Phe His Glu Gly Ala Ala Ala Leu Cys Gly Leu Val Tyr Leu Phe Ala
    75                  80                  85

CGC CTC CGC TAC TTC CAG GGC TAC GCG CGC TCC GCG CAG CTC AGG CTG         401
Arg Leu Arg Tyr Phe Gln Gly Tyr Ala Arg Ser Ala Gln Leu Arg Leu
 90                  95                 100                 105

GCA CCG CTG TAC GCG AGC GCG CGC GCC CTC TGG CTG CTG GTG GCG CTG         449
Ala Pro Leu Tyr Ala Ser Ala Arg Ala Leu Trp Leu Leu Val Ala Leu
                110                 115                 120

GCT GCG CTC GGC CTG CTC GCC CAC TTC CTC CCG GCC GCG CTG CGC GCC         497
Ala Ala Leu Gly Leu Leu Ala His Phe Leu Pro Ala Ala Leu Arg Ala
            125                 130                 135

GCG CTC CTC GGA CGG CTC CGG ACG CTG CTG CCG TGG GCC TGAGACCAAG          546
Ala Leu Leu Gly Arg Leu Arg Thr Leu Leu Pro Trp Ala
                140                 145                 150

GCCCCCGGGC CGACGGAGCC GGGAAAGAAG AGCCGGAGCC TCCAGCTGCC CCGGGGAGGG       606

GCGCTCGCTT CCGCATCCTA GTCTCTATCA TTAAAGTTCT AGTGACCGAG AAAAAAAAAA       666

AAAAAAAAAA AAACTCGAG                                                   685

(2) INFORMATION FOR SEQ ID NO:2:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Asp Glu Val Ala Leu Leu Ala Ala Val Thr Leu Leu Gly Val
  1               5                  10                  15

Leu Leu Gln Ala Tyr Phe Ser Leu Gln Val Ile Ser Ala Arg Arg Ala
             20                  25                  30

Phe Arg Val Ser Pro Pro Leu Thr Thr Gly Pro Pro Glu Phe Glu Arg
         35                  40                  45

Val Tyr Arg Ala Gln Val Asn Cys Ser Glu Tyr Phe Pro Leu Phe Leu
     50                  55                  60

Ala Thr Leu Trp Val Ala Gly Ile Phe Phe His Glu Gly Ala Ala Ala
 65                  70                  75                  80

Leu Cys Gly Leu Val Tyr Leu Phe Ala Arg Leu Arg Tyr Phe Gln Gly
             85                  90                  95

Tyr Ala Arg Ser Ala Gln Leu Arg Leu Ala Pro Leu Tyr Ala Ser Ala
            100                 105                 110

Arg Ala Leu Trp Leu Leu Val Ala Leu Ala Ala Leu Gly Leu Leu Ala
            115                 120                 125

His Phe Leu Pro Ala Ala Leu Arg Ala Ala Leu Leu Gly Arg Leu Arg
            130                 135                 140

Thr Leu Leu Pro Trp Ala
145                 150

(2) INFORMATION FOR SEQ ID NO:3:
```

(i) SEQUENCE CHARACTERISTICS:
       (A) LENGTH: 685 base pairs
       (B) TYPE: nucleic acid
       (C) STRANDEDNESS: double
       (D) TOPOLOGY: linear (ii) MOLECULE TYPE: cDNA (iv) ANTI-SENSE: YES (xi) SEQUENCE DESCRIPTION: SEQ ID NO:3:

```
CTCGAGTTTT TTTTTTTTTT TTTTTTTTTC TCGGTCACTA GAACTTTAAT GATAGAGACT      60

AGGATGCGGA AGCGAGCGCC CCTCCCCGGG GCAGCTGGAG GCTCCGGCTC TTCTTTCCCG     120

GCTCCGTCGG CCCGGGGGCC TTGGTCTCAG GCCCACGGCA GCAGCGTCCG GAGCCGTCCG     180

AGGAGCGCGG CGCGCAGCGC GGCCGGGAGG AAGTGGGCGA GCAGGCCGAG CGCAGCCAGC     240

GCCACCAGCA GCCAGAGGGC GCGCGCGCTC GCGTACAGCG GTGCCAGCCT GAGCTGCGCG     300

GAGCGCGCGT AGCCCTGGAA GTAGCGGAGG CGCGCGAACA GGTAGACCAG GCCGCACAGG     360

GCCGCCGCCC CTTCATGAAA GAAGATGCCG GCGACCCAGA GCGTGGCGAG GAACAGCGGG     420

AAGTACTCGC TGCAGTTCAC CTGGGCTCGG TAGACGCGCT CGAACTCGGG TGGGCCGGTG     480

GTGAGCGGCG GCGACACGCG GAAGGCCCTG CGCGCCGAGA TCACCTGCAG GGAGAAGTAG     540

GCTTGCAGCA GGACTCCCAG GAGGGTGACA GCAGCCAGTA GAGCTACCTC GTCCTTCATG     600

GTACCGTCGG TGTGGTGGCA CGGGCTGTGT GTGAAGGCGA GCTGGGAAC GCTTAGCCCC      660

GTCTGCTGCT CCTCGTGCCG AATTC                                          685
```

(2) INFORMATION FOR SEQ ID NO:4:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (synthetic)

(ix) FEATURE:
       (A) NAME/KEY: modified_base
       (B) LOCATION: 6
       (D) OTHER INFORMATION: /mod_base= i (ix) FEATURE:
       (A) NAME/KEY: modified_base
       (B) LOCATION: 12
       (D) OTHER INFORMATION: /mod_base= i (ix) FEATURE:
       (A) NAME/KEY: modified_base
       (B) LOCATION: 15
       (D) OTHER INFORMATION: /mod_base= i (ix) FEATURE:
       (A) NAME/KEY: modified_base
       (B) LOCATION: 18
       (D) OTHER INFORMATION: /mod_base= i (ix) FEATURE:
       (A) NAME/KEY: modified_base
       (B) LOCATION: 21
       (D) OTHER INFORMATION: /mod_base= i (ix) FEATURE:
       (A) NAME/KEY: modified_base
       (B) LOCATION: 24
       (D) OTHER INFORMATION: /mod_base= i (xi) SEQUENCE DESCRIPTION: SEQ ID NO:4:

ATGAANGATG ANGTNGCNCT NCTNGC                                                26

(2) INFORMATION FOR SEQ ID NO:5:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (synthetic)

(ix) FEATURE:
          (A) NAME/KEY: modified_base
          (B) LOCATION: 3
          (D) OTHER INFORMATION: /mod_base= i (ix) FEATURE:
          (A) NAME/KEY: modified_base
          (B) LOCATION: 9
          (D) OTHER INFORMATION: /mod_base= i (ix) FEATURE:
          (A) NAME/KEY: modified_base
          (B) LOCATION: 12
          (D) OTHER INFORMATION: /mod_base= i (ix) FEATURE:
          (A) NAME/KEY: modified_base
          (B) LOCATION: 15
          (D) OTHER INFORMATION: /mod_base= i (ix) FEATURE:
          (A) NAME/KEY: modified_base
          (B) LOCATION: 18
          (D) OTHER INFORMATION: /mod_base= i (xi) SEQUENCE DESCRIPTION: SEQ ID NO:5:

ACNCGGAANG CNATNCGNGC                                                       20

(2) INFORMATION FOR SEQ ID NO:6:

(i) SEQUENCE CHARACTERISTICS:
          (A) LENGTH: 105 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:6:

ATGAAGGATG AGGTGGCGCT GCTGGCTGCT GTCACCCTCC TGGGAGTCCT GCTGCAAGCC           60

TACTTCTCCC TGCAGGTGAT CTCGGCCCGC ATCGCCTTCC GCGTA                          105

(2) INFORMATION FOR SEQ ID NO:7:

(i) SEQUENCE CHARACTERISTICS:
          (A) LENGTH: 58 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:7:

CGAGATCACC TGCAGGGAGA AGTAGGCTTG CAGCAGGACT CCCAGGAGGG TGACAGCA             58

(2) INFORMATION FOR SEQ ID NO:8:

(i) SEQUENCE CHARACTERISTICS:

-continued

```
        (A) LENGTH: 30 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:8:

TGCAGCAGGA CTCCCAGGAG GGTGACAGCA                                             30

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:9:

CGAGATCACC TGCAGGGAGA AGTAGGCTTG                                              30

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:10:

GATCGAATTC ATGAAAGACG AAGTTGCTCT GCTGGCTGC                                    39

(2) INFORMATION FOR SEQ ID NO:11:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:11:

GATCGATGGA TCCATGAAGG ACGAGGTAGC TCTACTGGC                                    39

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:12:

GATCGAATTC GGATCCTCAG GCCCACGGCA GCAGCG                                       36
```

We claim:

1. A nucleic acid which comprises a DNA segment which encodes at least a portion of human leukotriene $C_4$ synthase, which nucleic acid is substantially free from nucleic acids not containing a DNA segment which encodes at least a portion of human $LTC_4$ synthase being selected from the group of:

(i) a nucleic acid sequence represented by nucleotides 7–679, inclusive, or a nucleic acid sequence represented by nucleotides 87–539, inclusive, of Sequence ID No. 1;

(ii) a nucleotide sequence which is complementary to a nucleotide sequence of (i);

(iii) fragments of (i) of (ii) which are at least 17 bases in length and which will selectively hybridize under stringent conditions, to a nucleic acid encoding human $LTC_4$ synthase; and (iv) nucleotide sequences which are at least about 17 bases in length and which will selectively hybridize, under stringent hybridization conditions, to a cDNA strand having a nucleic acid sequence represented by Sequence ID No. 1 or a nucleic acid sequence which is complementary to Sequence ID No. 1 or genomic DNA encoding human $LTC_4$ synthase.

2. A DNA expression vector for expression of $LTC_4$ synthase in a eukaryotic host cell, comprising (1) a promoter segment of a first gene, which segment comprises the promoter and transcription initiation site of the first gene, (2) a terminator segment of a second gene, which may be the same or different from the first gene, which terminator segment comprises a polyadenylation signal encoding and polyadenylation site encoding segments and a transcription termination signal, the terminator segment of the second gene being oriented, with respect to the direction of transcription from the promoter segment of the first gene, operatively for termination of transcription at said transcription termination site of the terminator segment; and (3) a DNA segment encoding human $LTC_4$ synthase which is oriented and positioned, between the promoter segment of the first gene and termination segment of the second gene, operatively for transcription of the $LTC_4$ synthase encoding DNA, the nucleotide sequence encoding the $LTC_4$ synthase being represented by nucleotides 87–536 inclusive of Sequence ID No. 1. or being a nucleotide sequence which encodes the $LTC_4$ synthase and which is capable of selectively hybridizing, under stringent conditions, to the complement of said nucleic acid sequence represented by nucleotides 87–536 inclusive of Sequence ID No. 1.

3. A DNA expression vector according to claim 2 which is a baculovirus *Autographa californica* nuclear polyhedrosis virus expression vector.

4. A DNA expression vector according to claim 3 wherein the promoter is the polyhedron promoter.

5. A DNA expression vector according to claim 3 which is pMON23962.

6. A DNA expression vector according to claim 2 which is capable of expression of $LTC_4$ synthase in a mammalian cell.

7. A DNA expression vector according to claim 2 which is capable of expression of $LTC_4$ synthase in a yeast cell.

8. A DNA expression vector for expression of $LTC_4$ synthase in a prokaryotic host cell, comprising (1) a promoter segment of a first gene, which segment comprises the promoter and transcription initiation, site of the first gene, (2) a ribosome binding site of a second gene, which may be the same as or different from the first gene, which ribosome binding site is effective for initiating translation in prokayotes, and (3) a DNA Segment encoding human $LTC_4$ synthase, the nucleotide sequence encoding the $LTC_4$ synthase being represented by nucleotides 87–539 inclusive of Sequence ID No. 1, or being a nucleotide sequence which encodes the $LTC_4$ synthase which is capable of selectively hybridizing, under stringent conditions, to the complement of said nucleic acid sequence represented by nucleotides 87–536 inclusive of Sequence ID No. 1, the promoter segment and the ribosome binding site being oriented and positioned operatively with respect to the $LTC_4$ synthase encoding DNA segment for expression of recombinant human $LTC_4$ synthase.

9. A eukaryotic host cell containing the DNA of claim 2.

10. An insect host cell containing a DNA according to claim 3.

11. A prokaryotic host cell containing the DNA of claim 8.

12. A nucleic acid according to claim 1 which is selected from the group consisting of a nucleic acid sequence represented by nucleotides 7–679, inclusive; a nucleic acid sequence represented by nucleotides 87–539, inclusive, of Sequence ID No. 1; and nucleic acids having a sequence which encode $LTC_4$ synthase and which are capable of selectively hybridizing, under stringent conditions, to a nucleic acid having a sequence which is complementary to the sequence represented by Sequence ID No. 1.

13. A nucleic acid according to claim 1 which is selected from the group consisting of a nucleic acid sequence represented by nucleotides 7–679, inclusive; and a nucleic acid sequence represented by nucleotides 87–539, inclusive, of Sequence ID No. 1.

14. A DNA expression vector according to claim 2 wherein the nucleic acid sequence encoding the $LTC_4$ synthase is represented by nucleotides 87–539 inclusive of Sequence ID No. 1.

15. A DNA expression vector according to claim 8 wherein the nucleic acid sequence encoding the $LTC_4$ synthase is represented by nucleotides 87–539 inclusive of Sequence ID No. 1.

* * * * *

UNITED STATES PATENT AND TRADEMARK OFFICE
CERTIFICATE OF CORRECTION

PATENT NO. : 5,952,210
DATED : September 14, 1999
INVENTOR(S) : DAVID PAUL CREELY ET AL.

It is certified that error appears in the above-identified patent and that said Letters Patent is hereby corrected as shown below:

ON THE TITLE PAGE [54]

The title, "LEUKOTIENE" should read --LEUKOTRIENE--.

ON THE TITLE PAGE [57]

Line 6, "LTC4" should read --$LTC_4$--.

COLUMN 1:

Line 3, "LEUKOTIENE" should read --LEUKOTRIENE--; and
Line 41, "synthases" should read --synthase--.

COLUMN 2:

Line 16, "LTC4" should read --$LTC_4$--; and
Line 50, "C4" should read --$C_4$--.

COLUMN 4:

Line 57, "double stranded" should read --double-stranded--; and
Line 66, "guanosine" should read --guanosine,--.

COLUMN 8:

Line 19, "(1980)." should read --(1980)).--; and
Line 55, "glyceralehyde-3-phosphate" should read --glyceraldehyde-3-phosphate--.

UNITED STATES PATENT AND TRADEMARK OFFICE
CERTIFICATE OF CORRECTION

PATENT NO.    : 5,952,210
DATED         : September 14, 1999
INVENTOR(S)   : DAVID PAUL CREELY ET AL.

It is certified that error appears in the above-identified patent and that said Letters Patent is hereby corrected as shown below:

COLUMN 9:

Line 15, "used" should read --be used--; and
    Line 67, "segment" should read --segments--.

COLUMN 10:

Line 32, "M)in" should read --M) in--;
    Line 34, "taurocholate,0.5%" should read
        --taurocholate, 0.5%--;
    Line 36, "LTC2" should read --$LTC_2$--.

COLUMN 11:

Line 37, "affect" should read --effect--.

COLUMN 13:

Line 20, "wahing" should read --washing--.

COLUMN 14:

Line 38, "demsity" should read --density--.

COLUMN 16:

Line 35, "gyratoty" should read --gyratory--.

COLUMN 17:

Line 15, "stratagene." should read --"Stratagene.--; and
    Line 35, "and and" should read --and--.

UNITED STATES PATENT AND TRADEMARK OFFICE
CERTIFICATE OF CORRECTION

PATENT NO. : 5,952,210

DATED : September 14, 1999

INVENTOR(S) : DAVID PAUL CREELY ET AL.

It is certified that error appears in the above-identified patent and that said Letters Patent is hereby corrected as shown below:

COLUMN 18:

Line 10, "6 µl mM" should read --6 µl 10 mM--; and
    Line 52, "suppliment" should read --supplement--.

COLUMN 19:

Line 54, "succesive" should read --successive--;
    Line 66, "[$\lambda^{32}$P]" should read --[$\gamma^{32}$P]--.

COLUMN 20:

Line 53, "supernatant" should read --supernatants--; and
    Line 56, "I 200298)" should read --#200298)--.

COLUMN 21:

Line 6, "pMON 23959." should read --pMON23959.--;
    Line 27, "supensions" should read --suspensions--;
    Line 49, "supended" should read --suspended--; and
    Line 55, "(seperately)" should read --(separately)--.

COLUMN 22:

Line 7, "added ," should read --added, --;
    Line 19, "completly" should read --completely--;
    Line 37, "Ban HI-digested" should read --Bam HI-digested--; and
    Line 58, "15" should be deleted.

UNITED STATES PATENT AND TRADEMARK OFFICE
CERTIFICATE OF CORRECTION

PATENT NO. : 5,952,210

DATED : September 14, 1999

INVENTOR(S) : DAVID PAUL CREELY ET AL.

It is certified that error appears in the above-identified patent and that said Letters Patent is hereby corrected as shown below:

COLUMN 23:

Line 3, "the the" should read --the--; and
Line 18, "supernatent" should read --supernatant--.

COLUMN 24:

Line 1, "facturers" should read --facturer's--.

COLUMN 33:

Line 2 "hybridize" should read --hybridize,--.

COLUMN 34:

Line 7, "Segment" should read --segment--.

Signed and Sealed this

Fourteenth Day of November, 2000

*Attest:*

Q. TODD DICKINSON

*Attesting Officer*   *Director of Patents and Trademarks*